(12) United States Patent
Roux et al.

(10) Patent No.: US 12,187,793 B2
(45) Date of Patent: Jan. 7, 2025

(54) SINGLE-DOMAIN ANTIBODY BINDING TO THE G PROTEIN ALPHA

(71) Applicants: CISBIO BIOASSAYS, Codolet (FR); CENTRE NATIONAL DE LA RECHERCHE SCIENTIFIQUE, Paris (FR); INSTITUT NATIONAL DE LA SANTE ET DE LA RECHERCHE MEDICALE (INSERM), Paris (FR)

(72) Inventors: Thomas Fabien Michel Roux, Nîmes (FR); Elodie Julie Dupuis, Caissargues (FR); Eric Jacques Christian Trinquet, Pont-Saint-Esprit (FR); Mélanie Da Silva, Saint-Macoux (FR); Camille S. Mailhac, Marseilles (FR); Patrick J M Chames, Marseilles (FR); Daniel Baty, Marseilles (FR); Julien Jean-Marius Soule, Montpellier (FR); Philippe Rondard, Saint-Gély-du-Fesc (FR); Jean-Philippe R. Pin, Montpellier (FR)

(73) Assignees: CISCIO BIOASSAYS, Codolet (FR); CENTRE NATIONAL DE LA RECHERCHE SCIENTIFIQUE, Paris (FR); INSTITUT NATIONAL DE LA SANTE ET DE LA RECHERCHE MEDICALE (INSERM), Paris (FR)

(*) Notice: Subject to any disclaimer, the term of this patent is extended or adjusted under 35 U.S.C. 154(b) by 1018 days.

(21) Appl. No.: 17/263,050

(22) PCT Filed: Jul. 26, 2019

(86) PCT No.: PCT/FR2019/051858
§ 371 (c)(1),
(2) Date: Jan. 25, 2021

(87) PCT Pub. No.: WO2020/021213
PCT Pub. Date: Jan. 30, 2020

(65) Prior Publication Data
US 2021/0309739 A1 Oct. 7, 2021

(30) Foreign Application Priority Data
Jul. 27, 2018 (FR) .................................. 1857026

(51) Int. Cl.
*C07K 16/28* (2006.01)

(52) U.S. Cl.
CPC ........ *C07K 16/28* (2013.01); *C07K 2317/565* (2013.01); *C07K 2317/567* (2013.01); *C07K 2317/569* (2013.01); *C07K 2317/92* (2013.01)

(58) Field of Classification Search
None
See application file for complete search history.

(56) References Cited

U.S. PATENT DOCUMENTS 6,448,377 B1 9/2002 Kobilka et al.
2008/0020994 A1 1/2008 Huang

FOREIGN PATENT DOCUMENTS

WO 2014201557 A1 12/2014

OTHER PUBLICATIONS

Colman et al in Research in Immunology (145(1):33-36, 1994) (Year: 1994).*
Abaza et al in Journal of Protein Chemistry (11(5):433-444, 1992) (Year: 1992).*
Lederman et al in Molecular Immunology (28:1171-1181, 1991) (Year: 1991).*
Li et al in PNAS (77:3211-3214, 1980) (Year: 1980).*
Yazhin et al. (Bioinformation 2021 vol. 17:439-445) (Year: 2021).*
Wu (Frontier in Immunology 2017 vol. 8, p. 1-13). (Year: 2017).*
Bowie Science 1990 vol. 247, p. 1306-1310 (Year: 1990).*
French Search Report issued in corresponding French Application No. 1857026 on Jul. 1, 2019, 2 pages.
International Search Report issued in corresponding International Application No. PCT/FR2019/051858 on Oct. 14, 2019, 3 pages.
Migyeong, J. et al., Engineering therapeutic antibodies targeting G-protein-coupled receptors, Experimental & Molecular Medicine, Feb. 1, 2016, vol. 48, No. 2, e207, 9 pages, DOI: 10.1038/emm.2015.105 XP055546956.

* cited by examiner

*Primary Examiner* — Changhwa J Cheu
(74) *Attorney, Agent, or Firm* — MH2 Technology Law Group, LLP

(57) ABSTRACT

The present invention relates to a single-domain antibody (sdAb) which binds to the G protein alpha, comprising an amino acid sequence consisting of 3 CDR regions (CDR1 to CDR3) and 4 hinge regions (FR1 to FR4) according to the following formula (I): FR1-CDR1-FR2-CDR2-FR3-CDR3-FR4 (I) and advantageously having a dissociation constant (Kd), measured in FRET, of less than 100 nM.

Figure 1:
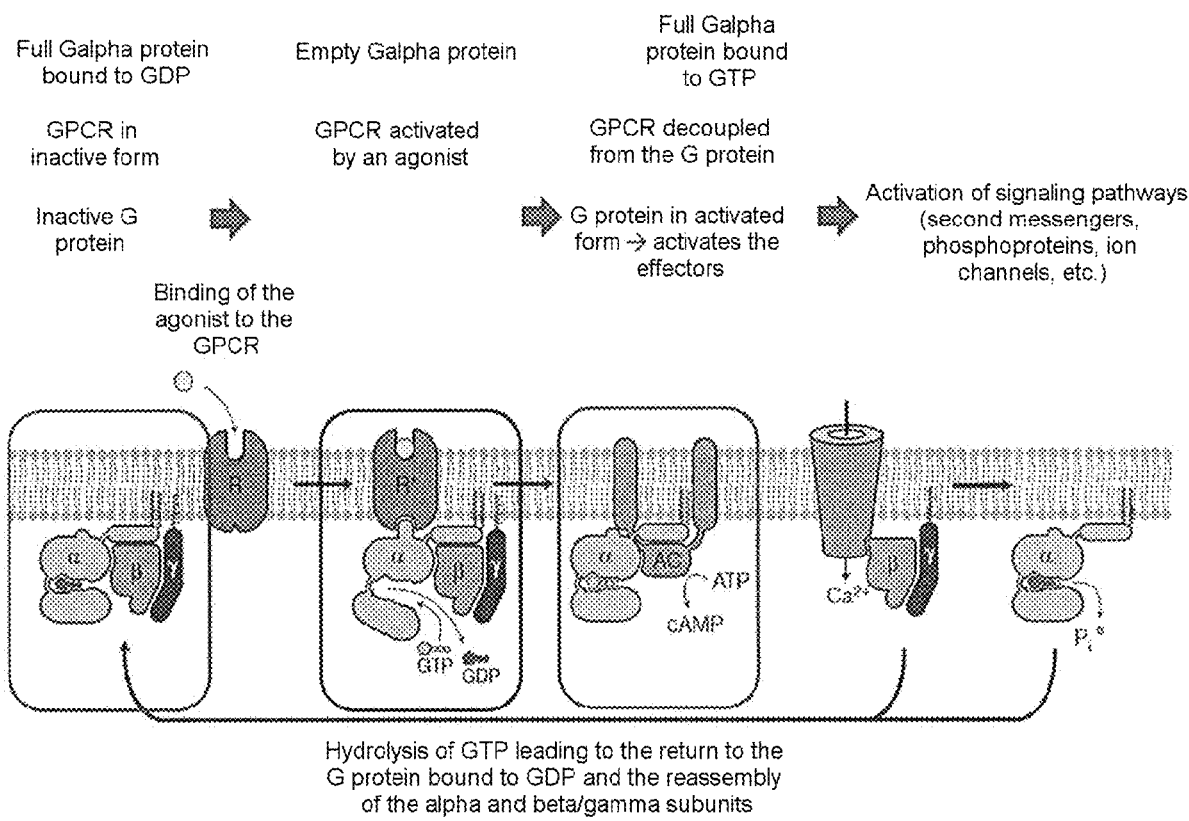

11 Claims, 11 Drawing Sheets
Specification includes a Sequence Listing.

SINGLE-DOMAIN ANTIBODY BINDING TO THE G PROTEIN ALPHA

CROSS-REFERENCE TO RELATED APPLICATION

This application is a U.S. National Stage Application of International Application No. PCT/FR2019/051858, filed on 26 Jul. 2019, which claims priority to French Patent Application No. 1857026, filed on 27 Jul. 2018, the entire disclosures of which are hereby incorporated by reference in their entireties.

SEQUENCE LISTING

The present application contains a Sequence Listing that has been submitted electronically in ASCII format and is hereby incorporated by reference in its entirety. Said ASCII copy, created on 23 Jul. 2024, is named 0177-0178 ST.25.txt and is 29,862 bytes in size.

FIELD OF THE INVENTION

The present invention relates to the field of antibodies and in particular to the field of single-domain antibodies (sdAb) which bind to the G protein alpha. sdAbs according to the invention are particularly suitable for use in FRET, for example in the form of heavy-chain antibodies (HcAbs) coupled to a molecule enabling their detection.

TECHNICAL BACKGROUND

"G protein-coupled receptors", or "GPCRs", are the membrane receptors most represented in mammals. They are the origin of a wide variety of cellular responses linked to various physiological processes (for example vision, olfaction, mediation of the action of numerous hormones, neuropeptides, etc.). They can be activated by ligands of very diverse natures, such as for example photons, ions, olfactory molecules, gustatory molecules, amino acids, nucleic acids, lipids, exogenous molecules such as cannabinoids, chemokines, or else hormones.

These receptors have seven transmembrane regions in the form of alpha helices each comprising between 22 and 24 amino acids. GPCRs can be classified in humans into 5 main families called Rhodopsin, Adhesion, Secretin, Glutamate, Frizzled/Taste2 (Fredriksson et al., 2003). GPCRs change functional conformation state depending on their level of activation by a ligand relative to a basal conformational state. When the GPCR is activated by the binding of a specific ligand, the change in conformation of the agonist-receptor complex enables activation of the heterotrimeric G protein.

G proteins are heterotrimeric proteins which transduce an activation signal from the GPCR by initiating biochemical reaction cascades having the purpose of transducing the signal from the exterior of the cell to the interior of the cell. G proteins are located on the inner face of the plasma membrane and are formed of three subunits ($\alpha$, $\beta$, $\gamma$). The alpha subunit is able to bind to guanine nucleotides, either GDP or GTP.

The commonly described mechanism of action of the GPCR and G protein is presented in FIG. 1 and summarized below:

in its inactive, rest state, the alpha subunit of the G protein is bound to the GDP nucleotide (full G protein bound to GDP);

after activation of the GPCR, the latter binds to the alpha subunit of the G protein and triggers a process of activation of the G protein, consisting of two steps: 1) the release of the GDP from the G protein to give an empty G protein, and the formation of an inactive GPCR/empty G protein complex, and 2) the attachment of GTP which leads to the formation of an active G protein, in GTP form (full G protein bound to GTP). In the first step, the G protein bound to the receptor is in a so-called "empty form". This state is described in the literature as being transient since it is described that the GTP nucleotide rapidly binds to the alpha subunit of the G protein. In addition, the beta/gamma subunits of the activated G protein dissociate from the alpha subunit;

the alpha subunit of the full G protein bound to GTP then binds to effectors to activate them. The effectors in turn activate signaling pathways, leading to a cellular response;

the GTP is then hydrolyzed to GDP by the alpha subunit of the G protein and the alpha subunit reassociates with the beta/gamma subunits to reform the full G protein bound to GDP (inactive state).

There are at least 17 different alpha subunits: Galpha i1, Galpha i2, Galpha 3, Galpha 01, Galpha o2, Galpha q, Galpha 12, Galpha 13, Galpha s, Galpha z, Galpha t1, Galpha t2, Galpha 11, Galpha 14, Galpha 15, Galpha 16 or Galpha gus.

Given the involvement of GPCRs in numerous signaling pathways, tools have been developed in the prior art for studying their activity, often with the aim of identifying novel ligands for these receptors which have a potential therapeutic activity. Mention may be made, by way of example of these tools, of the use of a non-hydrolyzable or slowly hydrolyzable radioactive derivative of GTP, particularly GTP-gamma-S, which binds to the G protein alpha when the receptor is activated. There are also recombinant systems based on the measurement of enzymatic activity such as luciferase, the expression of which is controlled by the second messengers produced by the activation of the receptor. Antibodies have also been synthesized to detect the activation of the GPCRs at the cell surface level (Damien Maurel. Oligomerisation des récepteurs couples aux protéines G: deux ou plus? Application des technologies de FRET en temps résolu au cas du récepteur GABAB. Biologie cellulaire. Montpellier 1 University, 2006. French). Reference may also be made to the patent EP2723764 B1, which proposes nano-antibodies which bind to the interface between the G protein alpha and the G protein beta/gamma, making it possible to stabilize the GPCR/G protein complex.

However, none of the prior art tools make it possible to specifically detect the alpha subunit of the G protein, much less an sdAb which binds to the G protein alpha, in particular for use in FRET. The present invention therefore advantageously proposes single-domain antibodies (sdAbs), for example heavy-chain antibodies (HcAbs) which bind to the G protein alpha (G protein alpha).

SUMMARY OF THE INVENTION

The present invention relates to a single-domain antibody (sdAb) which binds to the G protein alpha.

A first subject of the present invention relates to a single-domain antibody (sdAb) which binds to the G protein alpha, comprising an amino acid sequence consisting of 3 CDR regions (CDR1 to CDR3) and 4 hinge regions (FR1 to FR4) according to the following formula (I):

$$\text{FR1-CDR1-FR2-CDR2-FR3-CDR3-FR4} \qquad \text{(I)}$$

said antibody having a dissociation constant (Kd) for the full G protein alpha, measured in FRET, of less than 100 nM.

A second subject of the present invention relates to a single-domain antibody (sdAb) which binds to the G protein alpha, comprising an amino acid sequence consisting of 3 CDR regions (CDR1 to CDR3) and 4 hinge regions (FR1 to FR4) according to the following formula (I):

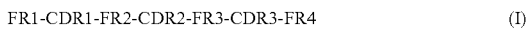

FR1-CDR1-FR2-CDR2-FR3-CDR3-FR4    (I)

in which:
CDR1 has at least 80% homology with an amino acid sequence chosen from SEQ ID NO: 1, SEQ ID NO: 9, SEQ ID NO: 17, SEQ ID NO: 25, SEQ ID NO: 33, SEQ ID NO: 41, SEQ ID NO: 49, SEQ ID NO: 57 and SEQ ID NO: 65;
CDR2 has at least 80% homology with an amino acid sequence chosen from SEQ ID NO: 2, SEQ ID NO: 10, SEQ ID NO: 18, SEQ ID NO: 26, SEQ ID NO: 34, SEQ ID NO: 42, SEQ ID NO: 50, SEQ ID NO: 58 and SEQ ID NO: 66; and
CDR3 has at least 80% homology with an amino acid sequence chosen from SEQ ID NO: 3, SEQ ID NO: 11, SEQ ID NO: 19, SEQ ID NO: 27, SEQ ID NO: 35, SEQ ID NO: 43, SEQ ID NO: 51, SEQ ID NO: 59 and SEQ ID NO: 67.

A third subject of the present invention relates to a nucleic acid sequence coding for the single-domain antibody (sdAb) according to the invention.

A fourth subject of the present invention relates to a recombinant vector comprising the nucleic acid sequence according to the invention.

A fifth subject of the present invention relates to a cell comprising the vector according to the invention or the nucleic acid sequence according to the invention.

Unless indicated otherwise, the terms "antibody according to the invention", "antibody of the invention", "sdAb according to the invention" or "sdAb of the invention" refer both to the first subject according to the invention and to the second subject according to the invention.

The subjects of the present invention are described more precisely below.

FIGURES

FIG. 1: Represents the mechanism of activation of a GPCR and the different stages of activation of the G protein alpha, namely the inactivated form (G protein alpha bound to GDP) and the activated form (Galpha protein bound to GTP).

Figure 2:
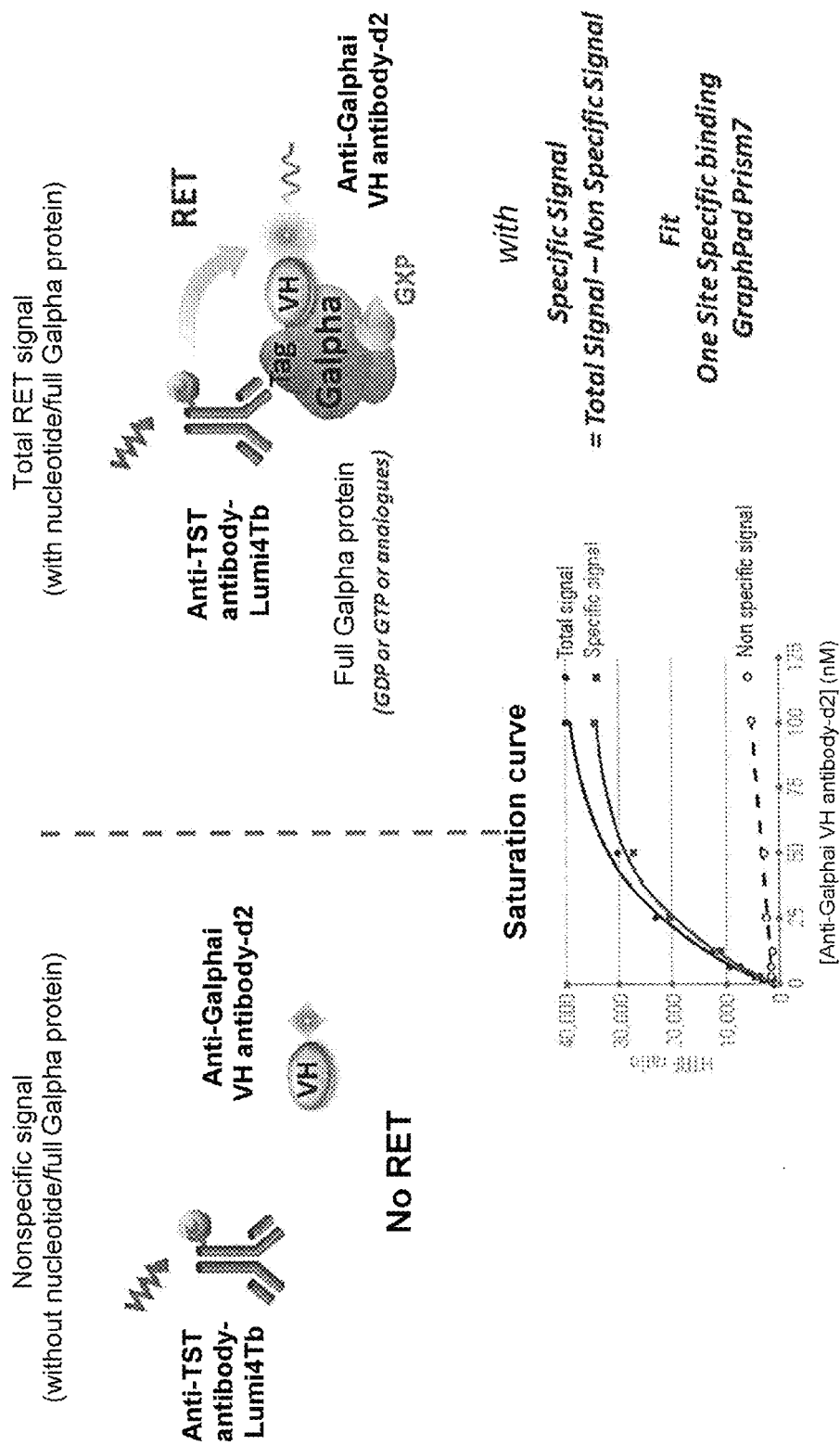

FIG. 2: Principle of the HTRF (TR-FRET) assay for determining the affinity (Kd) of the heavy chain variable domains (VH) implemented in FIGS. 3 to 11.

Figure 3:
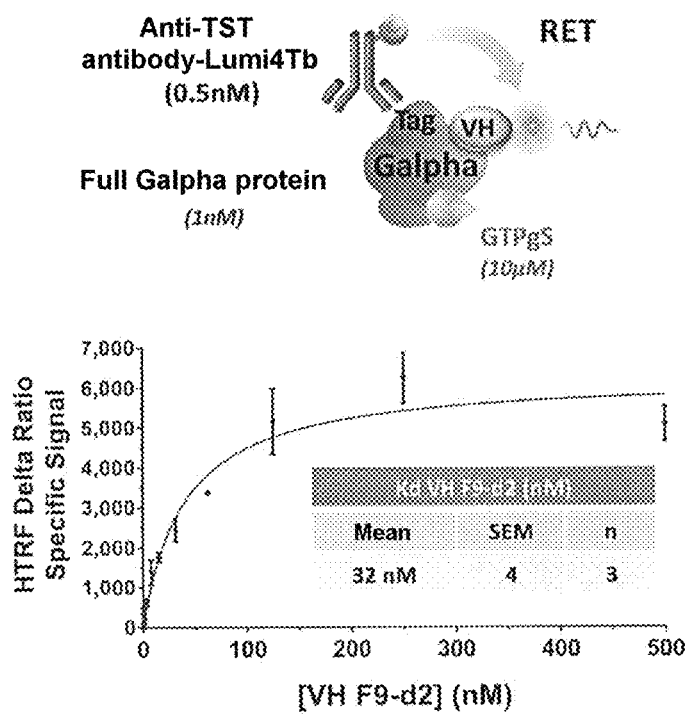

FIG. 3: Determination of the affinity (Kd) of VH F9 by TR-FRET assay. The principle of the assay detailed in FIG. 2 is used. The Galphai1 protein is loaded with an excess of GTPgS (10 μM). A Kd of 32 nM is obtained for the VH F9/Galphai1 protein interaction.

Figure 4:
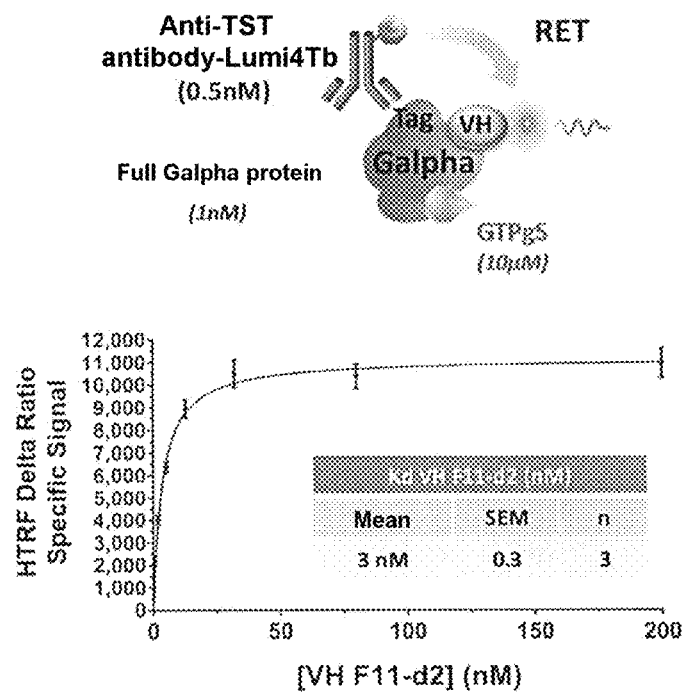

FIG. 4: Determination of the affinity (Kd) of VH F11 by TR-FRET assay. The assay principle detailed in FIG. 2 is used. The Galphai1 protein is loaded with an excess of GTPgS (10 μM). A Kd of 3 nM is obtained for the VH F11/Galphai1 protein interaction.

Figure 5:
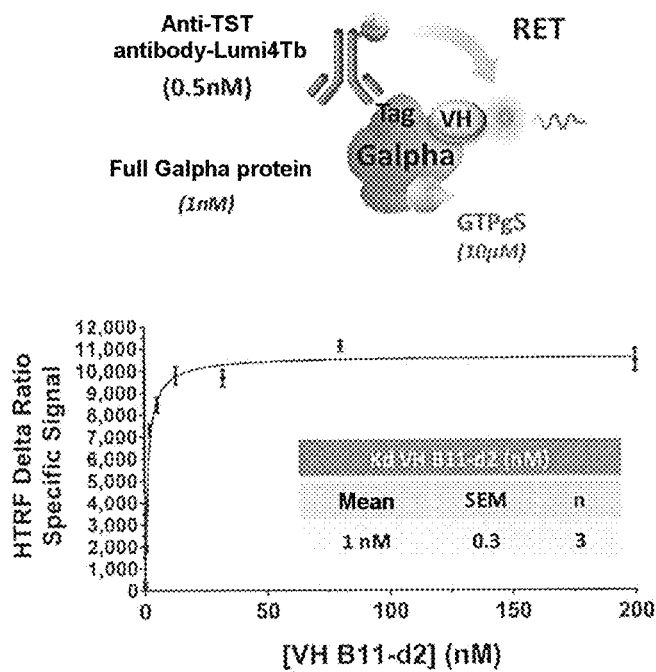

FIG. 5: Determination of the affinity (Kd) of VH B11 by TR-FRET assay. The assay principle detailed in FIG. 2 is used. The Galphai1 protein is loaded with an excess of GTPgS (10 μM). A Kd of 1 nM is obtained for the VH B11/Galphai1 protein interaction.

Figure 6:
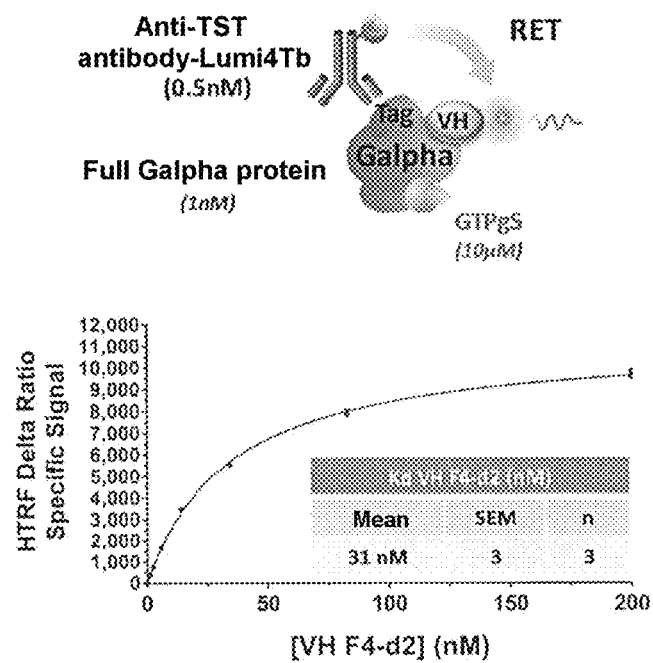

FIG. 6: Determination of the affinity (Kd) of VH F4 by TR-FRET assay. The assay principle detailed in FIG. 2 is used. The Galphai1 protein is loaded with an excess of GTPgS (10 μM). A Kd of 31 nM is obtained for the VH F4/Galphai1 protein interaction.

Figure 7:
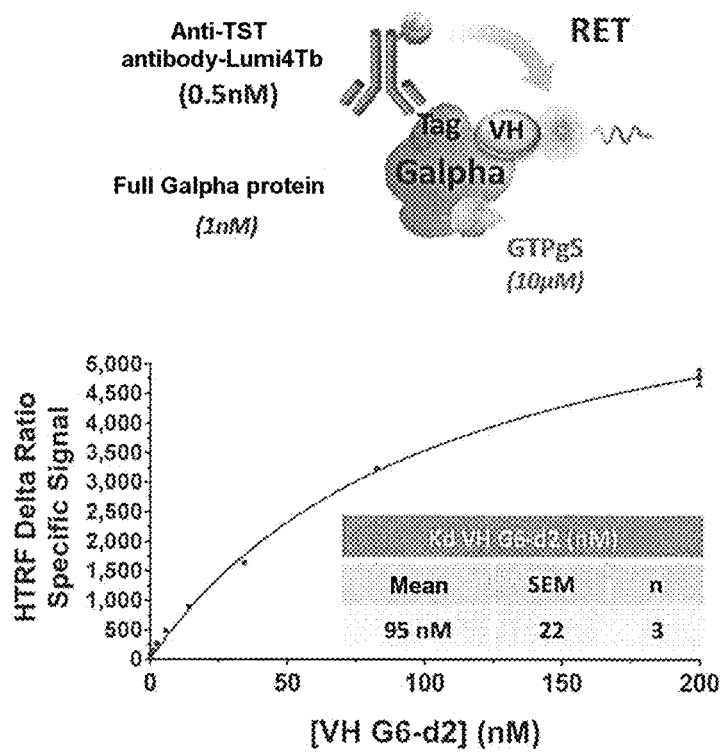

FIG. 7: Determination of the affinity (Kd) of VH G6 by TR-FRET assay. The assay principle detailed in FIG. 2 is used. The Galphai1 protein is loaded with an excess of GTPgS (10 μM). A Kd of 95 nM is obtained for the VH G6/Galphai1 protein interaction.

Figure 8:
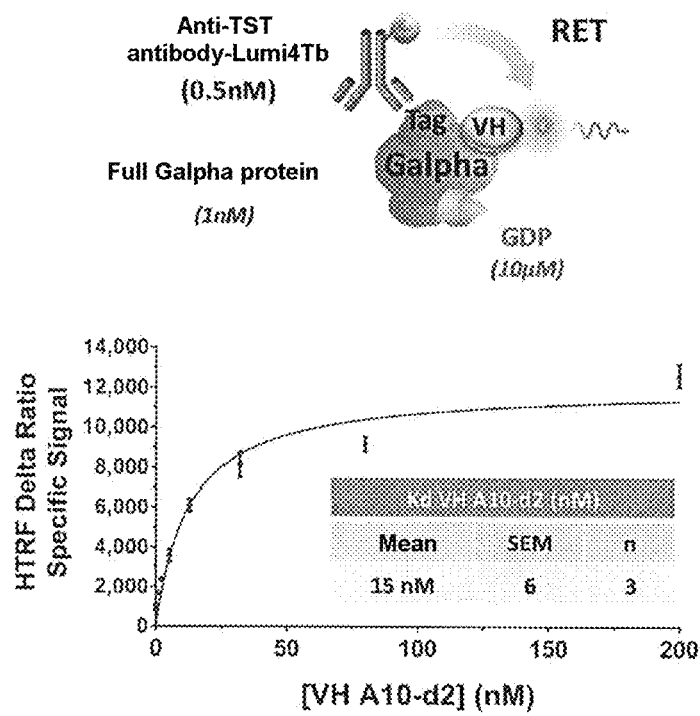

FIG. 8: Determination of the affinity (Kd) of VH A10 by TR-FRET assay. The assay principle detailed in FIG. 2 is used. The Galphai1 protein is loaded with an excess of GDP (10 μM). A Kd of 15 nM is obtained for the VH A10/Galphai1 protein interaction.

Figure 9:
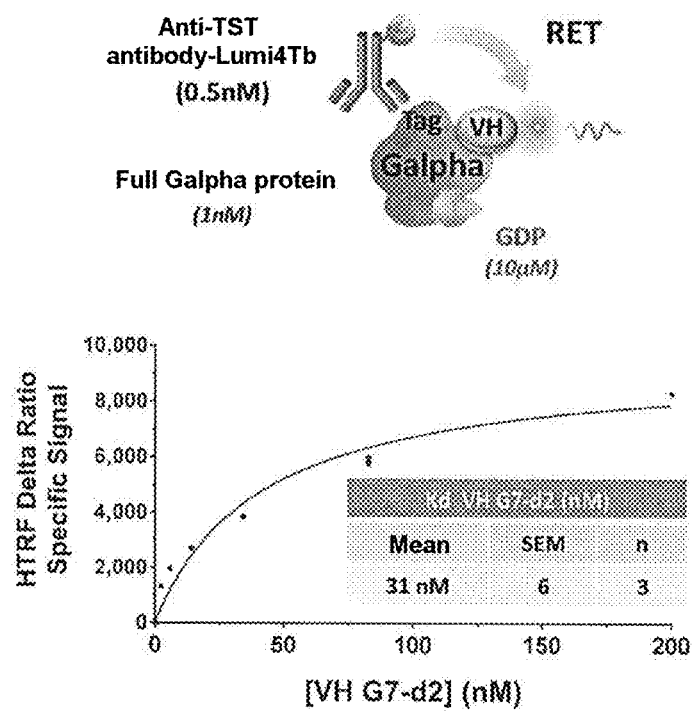

FIG. 9: Determination of the affinity (Kd) of VH G7 by TR-FRET assay. The assay principle detailed in FIG. 2 is used. The Galphai1 protein is loaded with an excess of GDP (10 μM). A Kd of 31 nM is obtained for the VH G7/Galphai1 protein interaction.

Figure 10:
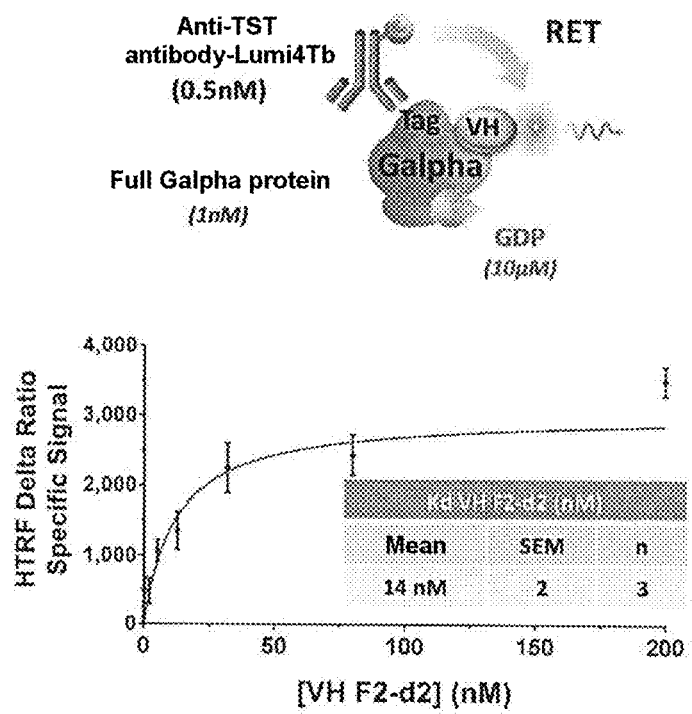

FIG. 10: Determination of the affinity (Kd) of VH F2 by TR-FRET assay. The assay principle detailed in FIG. 2 is used. The Galphai1 protein is loaded with an excess of GDP (10 μM). A Kd of 14 nM is obtained for the VH F2/Galphai1 protein interaction.

Figure 11:
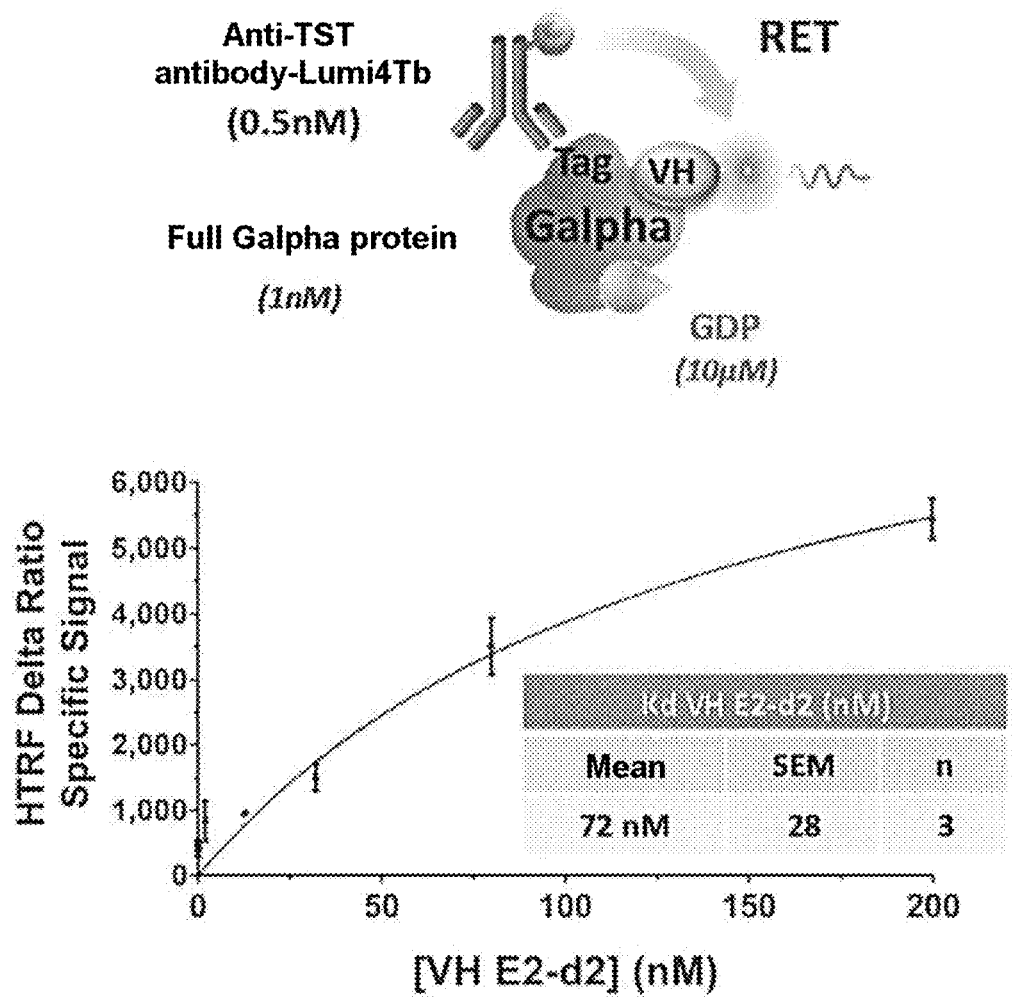

FIG. 11: Determination of the affinity (Kd) of VH E2 by TR-FRET assay. The assay principle detailed in FIG. 2 is used. The Galphai1 protein is loaded with an excess of GDP (10 μM). A Kd of 72 nM is obtained for the VH E2/Galphai1 protein interaction.

Figure 12:
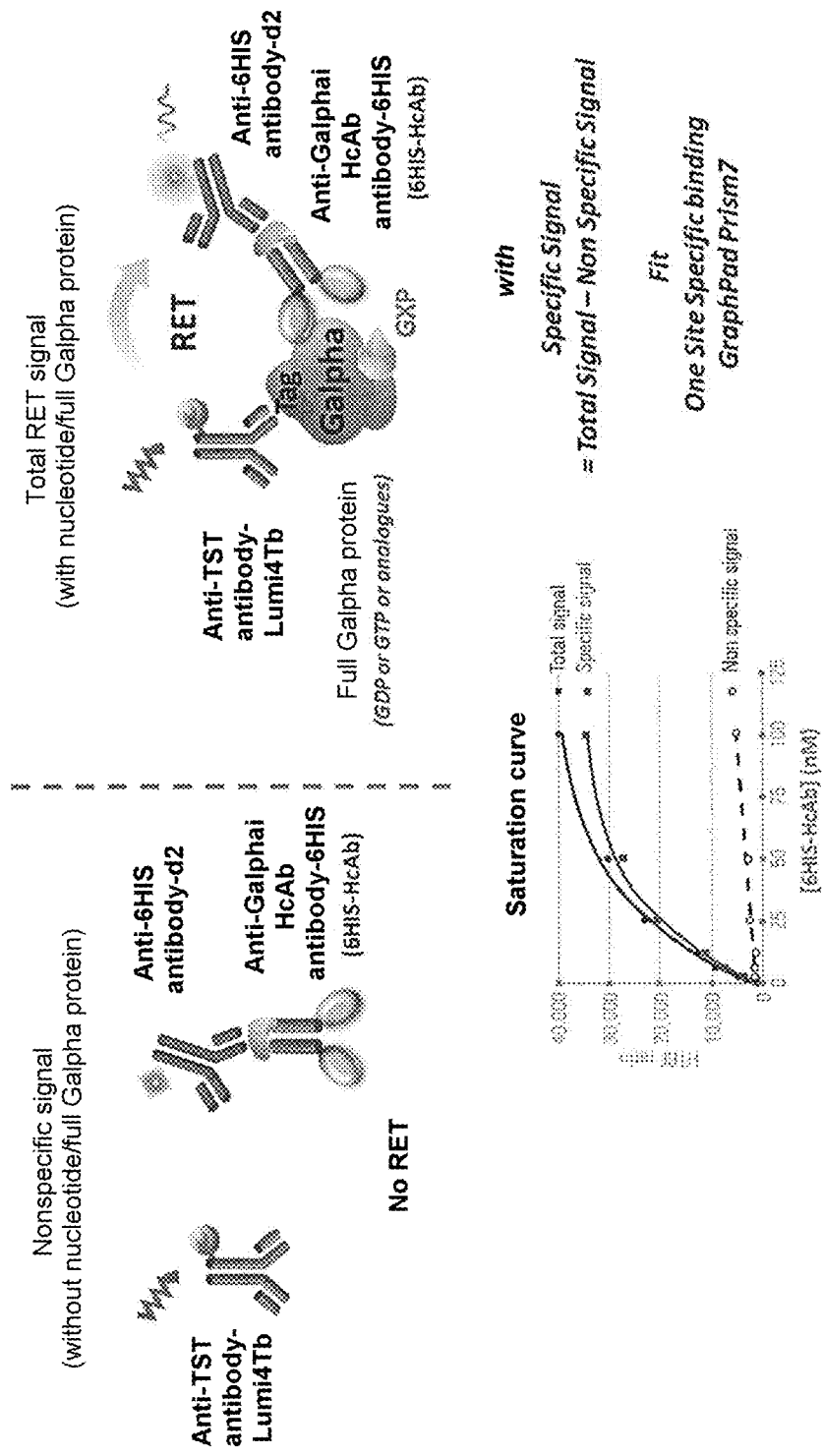

FIG. 12: Principle of the TR-FRET (HTRF) assay for determining the affinity (Kd) of VH-type HcAbs (VH HcAbs) implemented for FIGS. 13 to 16.

Figure 13:
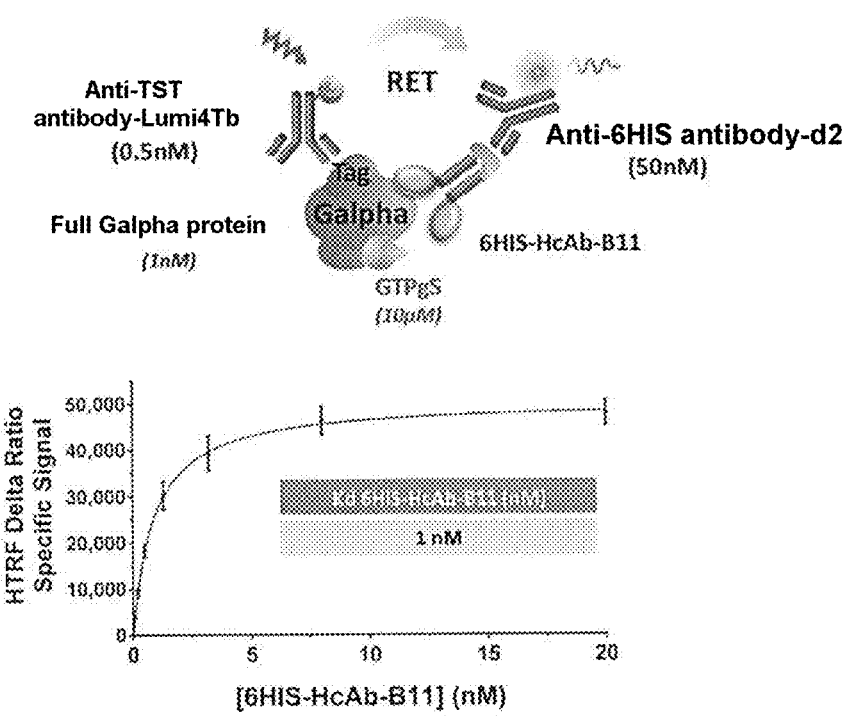

FIG. 13: Determination of the affinity (Kd) of HcAb-B11 by TR-FRET assay. The assay principle detailed in FIG. 12 is used. The Galphai1 protein is loaded with an excess of GTPgS (10 μM). A Kd of 1 nM is obtained for the HcAb-B11/Galphai1 protein interaction.

Figure 14:
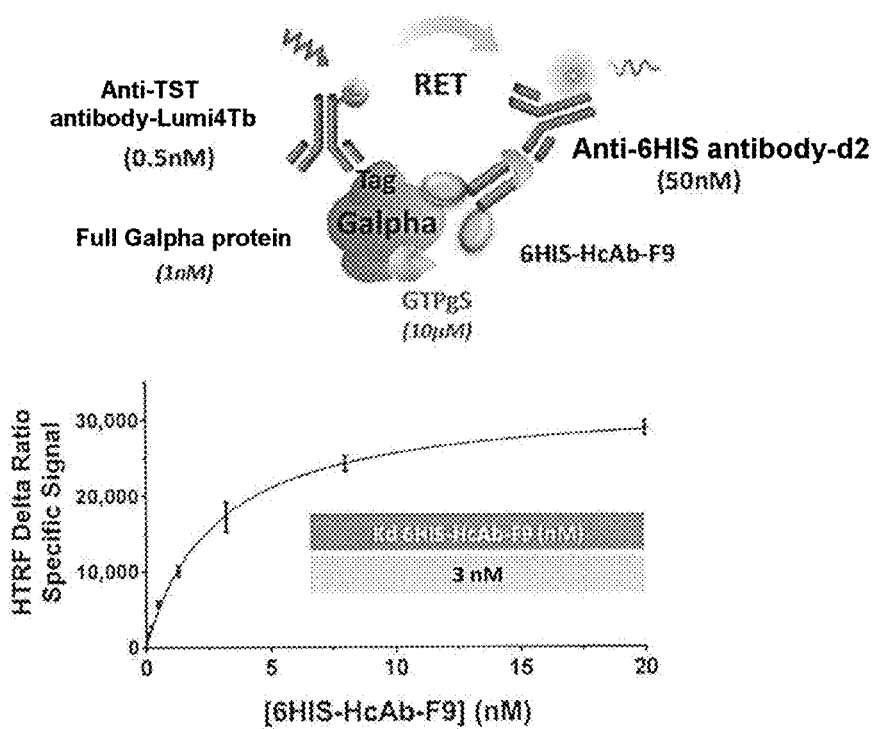

FIG. 14: Determination of the affinity (Kd) of HcAb-F9 by TR-FRET assay. The assay principle detailed in FIG. 12 is used. The Galphai1 protein is loaded with an excess of GTPgS (10 μM). A Kd of 3 nM is obtained for the HcAb-F9/Galphai1 protein interaction.

Figure 15:
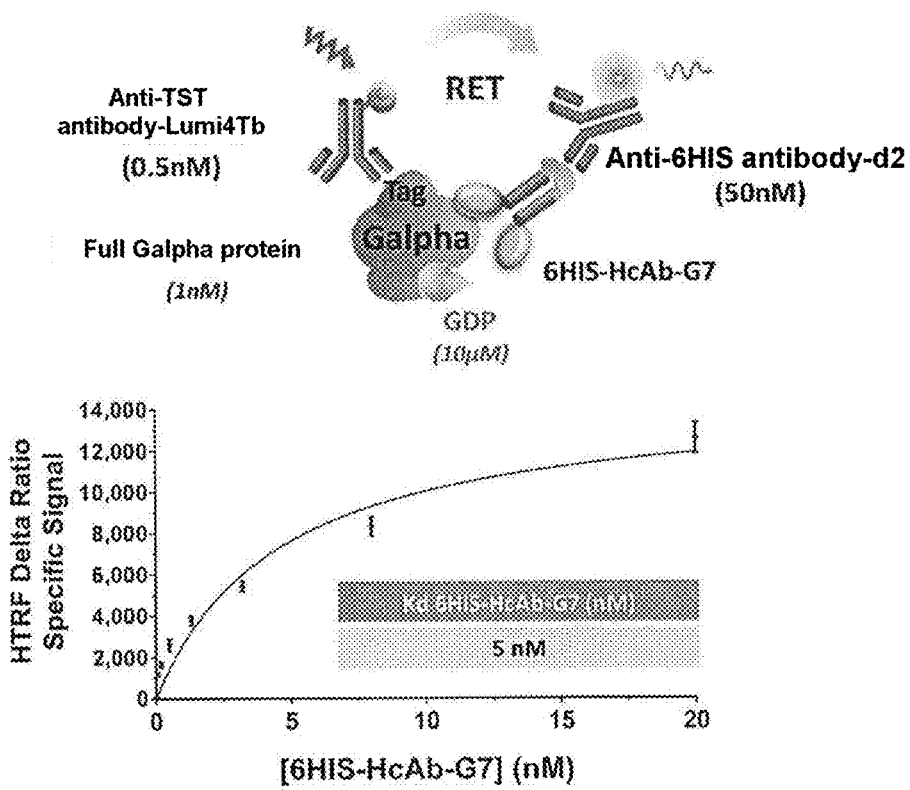

FIG. 15: Determination of the affinity (Kd) of HcAb-G7 by TR-FRET assay. The assay principle detailed in FIG. 12 is used. The Galphai1 protein is loaded with an excess of GDP (10 μM). A Kd of 5 nM is obtained for the HcAb-G7/Galphai1 protein interaction.

Figure 16:
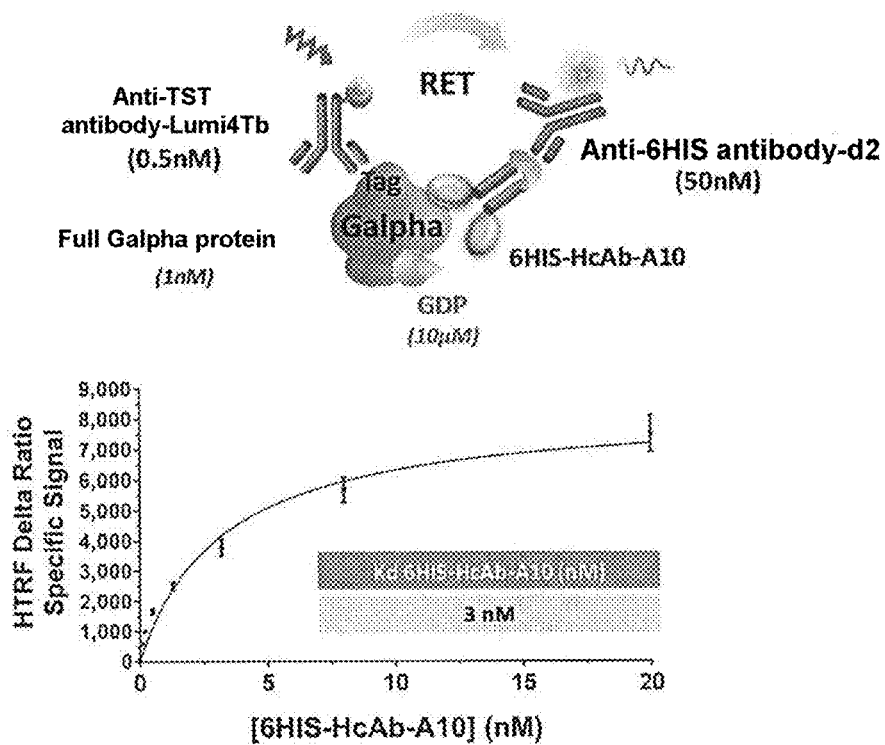

FIG. 16: Determination of the affinity (Kd) of HcAb-A10 by TR-FRET assay. The assay principle detailed in FIG. 12 is used. The Galphai1 protein is loaded with an excess of GDP (10 μM). A Kd of 3 nM is obtained for the HcAb-A10/Galphai1 protein interaction.

Figure 17:
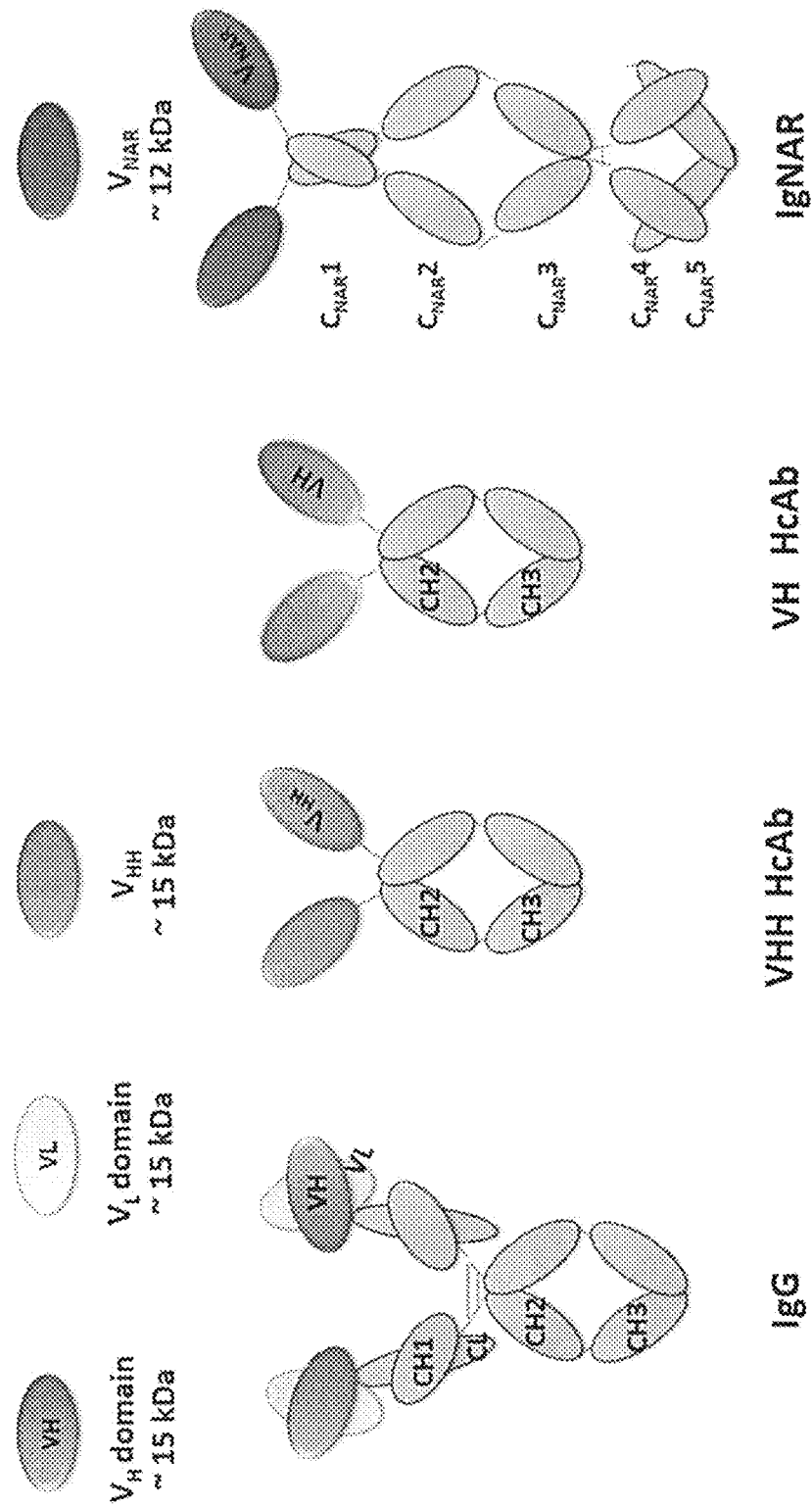

FIG. 17: Diagram of various possible forms of sdAb antibody according to the invention.

DETAILED DESCRIPTION OF THE INVENTION

The Applicants have developed single-domain antibodies (sdAbs) which bind to the G protein alpha with good affinity for the full G protein alpha. These sdAbs constitute particularly powerful tools as therapeutic agent, as diagnostic agent and/or as G protein alpha detection agent, in particular as G protein alpha detection agent in a FRET-type process.

Definitions

The terms "anti-G protein alpha antibody", "antibody which binds to the G protein alpha" and "antibody which binds specifically to the G protein alpha" are interchangeable and denote an antibody which binds to the G protein alpha with sufficient affinity for the antibody to be useful as a detection agent (for example for performing a FRET assay), a diagnostic agent and/or a therapeutic agent by targeting the G protein alpha.

"Antibody" is understood to mean a polypeptide coded by an immunoglobulin gene and capable of binding to an antigen. The term "antibody" is used herein in its broadest sense and encompasses diverse antibody structures which have the desired antigen-binding activity, including, but not limited to, monoclonal antibodies, polyclonal antibodies, multispecific antibodies (for example bispecific antibodies) and antibody fragments. "Conventional" antibodies—this is the case for example for G-type immunoglobulins (IgGs) in humans—are in the form of a tetramer comprising two pairs of identical polypeptide chains called light chains and two identical polypeptide chains called heavy chains. A variable domain is located at the N-terminal end of each of the chains ("VH" for the heavy chains and "VL" for the light chains) and the two variable domains VH and VL enable the recognition of the antigen. Each variable domain generally comprises 4 "hinge regions" (called FR1, FR2, FR3 and FR4) and 3 regions which are directly responsible for the binding with the antigen, referred to as "CDRs" (called CDR1, CDR2 and CDR3). In general, each variable domain has the following form: FR1-CDR1-FR2-CDR2-FR3-CDR3-FR4. Generally—this is the case for example for IgGs in humans—the binding to the antigen is performed by a pair of two variable domains (i.e. a light chain variable domain VL and a heavy chain variable domain VH), that is to say that 6 CDRs are involved in the formation of one antigen-binding site.

Conversely, for single-domain antibodies, only 3 CDRs are involved in the formation of an antigen-binding site. Thus, the antigen-binding site of a single-domain antibody is formed by 3 CDRs. Therefore, the terms "single-domain antibody" and "sdAb" are interchangeable and refer to an antibody in which the binding to the antigen is performed by a single variable domain. An sdAb may be i) an antibody comprising or consisting of a heavy chain variable domain (VH) or a fragment thereof capable of binding to the antigen, which binds to the antigen independently of any other variable domain, ii) an antibody comprising or consisting of a light chain variable domain (VL) or a fragment thereof capable of binding to the antigen, which binds to the antigen independently of any other variable domain, or iii) an antibody comprising or consisting of a $V_H$H-type heavy chain variable domain ($V_H$H) or a fragment thereof capable of binding to the antigen, which binds to the antigen independently of any other variable domain.

"VH-type heavy-chain antibody" or "VH HcAb" is understood to mean an antibody consisting of two heavy chains each comprising a VH-type variable domain. In particular, each heavy chain consists of the CH2 and CH3 fragments, and of said VH-type variable domain.

"$V_H$H-type heavy-chain antibody" or "$V_H$H HcAb" is understood to mean an antibody consisting of two heavy chains each comprising a $V_H$H-type variable domain. In particular, each heavy chain consists of the CH2 and CH3 fragments, and of said $V_H$H-type variable domain.

For the purposes of the invention, the terms "full G protein alpha" or "full form of the G protein alpha" denote a G protein alpha bound to GTP, to GDP or to an analog of these, for example to non-hydrolyzable or slowly hydrolyzable GTP. These terms thus denote the G protein alpha bound to GDP or to an analog of GDP ("G protein alpha bound to GDP") or the G protein alpha bound to GTP or to an analog of GTP, for example to non-hydrolyzable or slowly hydrolyzable GTP ("G protein alpha bound to GTP"). The full G protein alpha (G protein alpha bound to GDP or G protein alpha bound to GTP) is represented in FIG. 1.

The term "GDP" denotes guanosine diphosphate.
The term "GTP" denotes guanosine triphosphate.
The term "non-hydrolyzable or slowly hydrolyzable GTP" denotes an analog of GTP which is not hydrolyzed or is only slightly hydrolyzed to GDP. Mention may be made, for example, of GTPgammaS (also known under the acronyms "GTPgS" and "GTPγS") (CAS no. 37589-80-3), of GppNHp (CAS no. 148892-91-5) or of GppCp (CAS no. 10470-57-2).

For the purposes of the invention, the terms "empty G protein alpha" or "empty form of the G protein alpha" denote a G protein alpha which is not bound to GTP or to GDP. The empty G protein alpha is described in the literature as a transient state between the G protein alpha bound to GDP and the G protein alpha bound to GTP. The empty G protein alpha is represented in FIG. 1.

The term "affinity" refers to the force of all of the non-covalent interactions between a molecule, for example an sdAb, and its partner, for example an antigen such as the full G protein alpha. Affinity is generally represented by the dissociation constant (Kd). The dissociation constant (Kd) can be measured by well-known methods, for example by FRET or SPR.

The term "FRET" ("Fluorescence Resonance Energy Transfer") denotes the transfer of energy between two fluorescent molecules. FRET is defined as a non-radiative transfer of energy resulting from a dipole-dipole interaction between an energy donor and an energy acceptor. This physical phenomenon requires energy compatibility between these molecules. This means that the emission spectrum of the donor has to overlap, at least partially, the absorption spectrum of the acceptor. According to Förster's theory, FRET is a process which depends on the distance separating the two molecules, donor and acceptor: when these molecules are close to each other, a FRET signal will be emitted. Within the context of the present invention, the dissociation constant (Kd) is measured by FRET, for example as described in the examples.

For the purposes of the present invention, the "homology" is calculated by comparing two sequences aligned in a comparison window. The alignment of the sequences makes it possible to determine the number of positions (nucleotides or amino acids) which are common to the two sequences in the comparison window. The number of common positions is then divided by the total number of positions in the comparison window and multiplied by 100 in order to obtain the percentage of homology. The determination of the percentage of sequence homology can be carried out manually or using well-known computer programs.

"Purified" and "isolated", referring to an antibody according to the invention, are understood to mean that the antibody is present in the substantial absence of other biological macromolecules of the same type. The term "purified" as used herein means preferably at least 75% by weight, more preferably at least 85% by weight, more preferably still at least 95% by weight, and most preferably at least 98% by weight of antibody, relative to all of the macromolecules present.

sdAb Antibody

A first subject of the invention relates to a single-domain antibody (sdAb) which binds to the G protein alpha, comprising an amino acid sequence consisting of 3 complementarity-determining regions, "CDRs", (CDR1 to CDR3) and 4 hinge regions, "FRs", (FR1 to FR4) according to the following formula (I):

FR1-CDR1-FR2-CDR2-FR3-CDR3-FR4          (I)

having a dissociation constant (Kd) for the full G protein alpha, measured in FRET, of less than 100 nM.

According to the first subject, the sdAb binds to the full G protein alpha (either the G protein alpha bound to GTP or one of its analogs or the G protein alpha bound to GDP or one of its analogs) with a dissociation constant (Kd) measured in FRET of less than 100 nM, for example an affinity constant of less than 75 nM, less than 50 nM, less than 25 nM or else less than 10 nM, for example between 1 and 10 nM, between 10 and 100 nM, between 10 and 75 nM or between 10 and 50 nM.

According to the first subject, the sdAb can be obtained by immunization of a camelid comprising the administration of a full G protein alpha alone or in combination with an adjuvant such as for example an aluminum salt, Freund's adjuvant or a mineral oil. The administration can be done via the subcutaneous, intravenous, intramuscular or intraperitoneal route, preferably via the subcutaneous route, at a dose of between 10 µg and 10 mg. Said administration can be repeated several times, each administration being able to be spaced apart by one or more days in order to obtain an optimal immune response. The antibodies generated can then be recovered from peripheral blood mononuclear cells via conventional purification techniques known to those skilled in the art, for example by performing reverse transcription (RT-PCR) of the mRNAs coding for this antibody in order to obtain cDNAs which will then be cloned within a vector before being selected by "phage display library" using the full G protein alpha fixed on an ELISA plate.

In particular, the antibodies according to the invention can be obtained by performing the protocol described in Example 1.

In a particular embodiment of the first subject of the invention:
  CDR1 has at least 80% homology, preferably at least 90% homology, for example at least 95% homology, at least 96%, at least 97%, at least 98%, at least 99% or even 100% homology with an amino acid sequence chosen from SEQ ID NO: 1, SEQ ID NO: 9, SEQ ID NO: 17, SEQ ID NO: 25, SEQ ID NO: 33, SEQ ID NO: 41, SEQ ID NO: 49, SEQ ID NO: 57 and SEQ ID NO: 65;
  CDR2 has at least 80% homology, preferably at least 90% homology, for example at least 95% homology, at least 96%, at least 97%, at least 98%, at least 99% or even 100% homology with an amino acid sequence chosen from SEQ ID NO: 2, SEQ ID NO: 10, SEQ ID NO: 18, SEQ ID NO: 26, SEQ ID NO: 34, SEQ ID NO: 42, SEQ ID NO: 50, SEQ ID NO: 58 and SEQ ID NO: 66; and
  CDR3 has at least 80% homology, preferably at least 90% homology, for example at least 95% homology, at least 96%, at least 97%, at least 98%, at least 99% or even 100% homology with an amino acid sequence chosen from SEQ ID NO: 3, SEQ ID NO: 11, SEQ ID NO: 19, SEQ ID NO: 27, SEQ ID NO: 35, SEQ ID NO: 43, SEQ ID NO: 51, SEQ ID NO: 59 and SEQ ID NO: 67.

The amino acid sequences of CDR1, CDR2 and CDR3 can easily be combined with one another in order to comply with formula (I). Those skilled in the art know how to determine without difficulty the extent to which these sequences can be combined in order to obtain sdAbs according to the invention having the desired dissociation constant (Kd).

A second subject of the present invention relates to a single-domain antibody (sdAb) which binds to the G protein alpha, comprising an amino acid sequence consisting of 3 CDR regions (CDR1 to CDR3) and 4 hinge regions (FR1 to FR4) according to the following formula (I):

FR1-CDR1-FR2-CDR2-FR3-CDR3-FR4          (I)

in which:
  CDR1 has at least 80% homology, preferably at least 90% homology, for example at least 95% homology, at least 96%, at least 97%, at least 98%, at least 99% or even 100% homology with an amino acid sequence chosen from SEQ ID NO: 1, SEQ ID NO: 9, SEQ ID NO: 17, SEQ ID NO: 25, SEQ ID NO: 33, SEQ ID NO: 41, SEQ ID NO: 49, SEQ ID NO: 57 and SEQ ID NO: 65;
  CDR2 has at least 80% homology, preferably at least 90% homology, for example at least 95% homology, at least 96%, at least 97%, at least 98%, at least 99% or even 100% homology with an amino acid sequence chosen from SEQ ID NO: 2, SEQ ID NO: 10, SEQ ID NO: 18, SEQ ID NO: 26, SEQ ID NO: 34, SEQ ID NO: 42, SEQ ID NO: 50, SEQ ID NO: 58 and SEQ ID NO: 66; and
  CDR3 has at least 80% homology, preferably at least 90% homology, for example at least 95% homology, at least 96%, at least 97%, at least 98%, at least 99% or even 100% homology with an amino acid sequence chosen from SEQ ID NO: 3, SEQ ID NO: 11, SEQ ID NO: 19, SEQ ID NO: 27, SEQ ID NO: 35, SEQ ID NO: 43, SEQ ID NO: 51, SEQ ID NO: 59 and SEQ ID NO: 67.

The G protein alpha may be of human or animal origin. Advantageously, the sdAb according to the invention binds to the Galphai protein (Gai), for example the Galphai1 protein, the Galphai2 protein or the Galphai3 protein. The Galphai1 protein of human origin bears the UniProt identifier P63096-1 for the isoform 1 and the UniProt identifier P63096-2 for the isoform 2. The gene coding for the Galphai1 protein of human origin is known under the name "GNAI1" (Gene ID: 2770, NCBI).

The sdAb according to the invention may exist in different forms. It may for example be a heavy chain variable domain (VH), a $V_H$H-type heavy chain variable domain ($V_H$H), a VH-type heavy-chain antibody (VH HcAb), a $V_H$H-type heavy-chain antibody ($V_H$H HcAb), a cartilaginous fish-derived anti-immunoglobulin new antigen receptor IgG heavy-chain antibody (Ig NAR) or else an Ig NAR variable domain (V-NAR). Examples of antibody structures according to the invention are presented in FIG. 17.

In a preferred embodiment of the antibody according to the invention:
  CDR1 has at least 80% homology, preferably at least 90% homology, for example at least 95% homology, at least 96%, at least 97%, at least 98%, at least 99% or even 100% homology with SEQ ID NO: 1, CDR2 has at least 80% homology, preferably at least 90% homology, for example at least 95% homology, at least 96%, at least 97%, at least 98%, at least 99% or even 100% homology with SEQ ID NO: 2 and CDR3 has at least 80% homology, preferably at least 90% homology, for example at least 95% homology, at least 96%, at least 97%, at least 98%, at least 99% or even 100% homology with SEQ ID NO: 3;
  CDR1 has at least 80% homology, preferably at least 90% homology, for example at least 95% homology, at least 96%, at least 97%, at least 98%, at least 99% or even 100% homology with SEQ ID NO: 9, CDR2 has at least 80% homology, preferably at least 90% homology, for example at least 95% homology, at least 96%, at least 97%, at least 98%, at least 99% or even 100% homology with SEQ ID NO: 10 and CDR3 has at least 80% homology, preferably at least 90% homology, for example at least 95% homology, at least 96%, at least 97%, at least 98%, at least 99% or even 100% homology with SEQ ID NO: 11;

CDR1 has at least 80% homology, preferably at least 90% homology, for example at least 95% homology, at least 96%, at least 97%, at least 98%, at least 99% or even 100% homology with SEQ ID NO: 17, CDR2 has at least 80% homology, preferably at least 90% homology, for example at least 95% homology, at least 96%, at least 97%, at least 98%, at least 99% or even 100% homology with SEQ ID NO: 18 and CDR3 has at least 80% homology, preferably at least 90% homology, for example at least 95% homology, at least 96%, at least 97%, at least 98%, at least 99% or even 100% homology with SEQ ID NO: 19;

CDR1 has at least 80% homology, preferably at least 90% homology, for example at least 95% homology, at least 96%, at least 97%, at least 98%, at least 99% or even 100% homology with SEQ ID NO: 25, CDR2 has at least 80% homology, preferably at least 90% homology, for example at least 95% homology, at least 96%, at least 97%, at least 98%, at least 99% or even 100% homology with SEQ ID NO: 26 and CDR3 has at least 80% homology with SEQ ID NO: 27;

CDR1 has at least 80% homology, preferably at least 90% homology, for example at least 95% homology, at least 96%, at least 97%, at least 98%, at least 99% or even 100% homology with SEQ ID NO: 33, CDR2 has at least 80% homology, preferably at least 90% homology, for example at least 95% homology, at least 96%, at least 97%, at least 98%, at least 99% or even 100% homology with SEQ ID NO: 34 and CDR3 has at least 80% homology, preferably at least 90% homology, for example at least 95% homology, at least 96%, at least 97%, at least 98%, at least 99% or even 100% homology with SEQ ID NO: 35;

CDR1 has at least 80% homology, preferably at least 90% homology, for example at least 95% homology, at least 96%, at least 97%, at least 98%, at least 99% or even 100% homology with SEQ ID NO: 41, CDR2 has at least 80% homology, preferably at least 90% homology, for example at least 95% homology, at least 96%, at least 97%, at least 98%, at least 99% or even 100% homology with SEQ ID NO: 42 and CDR3 has at least 80% homology, preferably at least 90% homology, for example at least 95% homology, at least 96%, at least 97%, at least 98%, at least 99% or even 100% homology with SEQ ID NO: 43;

CDR1 has at least 80% homology, preferably at least 90% homology, for example at least 95% homology, at least 96%, at least 97%, at least 98%, at least 99% or even 100% homology with SEQ ID NO: 49, CDR2 has at least 80% homology, preferably at least 90% homology, for example at least 95% homology, at least 96%, at least 97%, at least 98%, at least 99% or even 100% homology with SEQ ID NO: 50 and CDR3 has at least 80% homology, preferably at least 90% homology, for example at least 95% homology, at least 96%, at least 97%, at least 98%, at least 99% or even 100% homology with SEQ ID NO: 51;

CDR1 has at least 80% homology, preferably at least 90% homology, for example at least 95% homology, at least 96%, at least 97%, at least 98%, at least 99% or even 100% homology with SEQ ID NO: 57, CDR2 has at least 80% homology, preferably at least 90% homology, for example at least 95% homology, at least 96%, at least 97%, at least 98%, at least 99% or even 100% homology with SEQ ID NO: 58 and CDR3 has at least 80% homology, preferably at least 90% homology, for example at least 95% homology, at least 96%, at least 97%, at least 98%, at least 99% or even 100% homology with SEQ ID NO: 59; or CDR1 has at least 80% homology, preferably at least 90% homology, for example at least 95% homology, at least 96%, at least 97%, at least 98%, at least 99% or even 100% homology with SEQ ID NO: 65, CDR2 has at least 80% homology, preferably at least 90% homology, for example at least 95% homology, at least 96%, at least 97%, at least 98%, at least 99% or even 100% homology with SEQ ID NO: 66 and CDR3 has at least 80% homology, preferably at least 90% homology, for example at least 95% homology, at least 96%, at least 97%, at least 98%, at least 99% or even 100% homology with SEQ ID NO: 67.

In a preferred embodiment of the antibody according to the invention:

FR1 has at least 80% homology, preferably at least 90% homology, for example at least 95% homology, at least 96%, at least 97%, at least 98%, at least 99% or even 100% homology with an amino acid sequence chosen from SEQ ID NO: 5, SEQ ID NO: 12, SEQ ID NO: 20, SEQ ID NO: 28, SEQ ID NO: 36, SEQ ID NO: 44, SEQ ID NO: 52, SEQ ID NO: 60 and SEQ ID NO: 68;

FR2 has at least 80% homology, preferably at least 90% homology, for example at least 95% homology, at least 96%, at least 97%, at least 98%, at least 99% or even 100% homology with an amino acid sequence chosen from SEQ ID NO: 6, SEQ ID NO: 13, SEQ ID NO: 21, SEQ ID NO: 29, SEQ ID NO: 37, SEQ ID NO: 45, SEQ ID NO: 53, SEQ ID NO: 61 and SEQ ID NO: 69; and FR3 has at least 80% homology, preferably at least 90% homology, for example at least 95% homology, at least 96%, at least 97%, at least 98%, at least 99% or even 100% homology with an amino acid sequence chosen from SEQ ID NO: 7, SEQ ID NO: 14, SEQ ID NO: 22, SEQ ID NO: 30, SEQ ID NO: 38, SEQ ID NO: 46, SEQ ID NO: 54, SEQ ID NO: 62 and SEQ ID NO: 70; and FR4 has at least 80% homology, preferably at least 90% homology, for example at least 95% homology, at least 96%, at least 97%, at least 98%, at least 99% or even 100% homology with an amino acid sequence chosen from SEQ ID NO: 8, SEQ ID NO: 15, SEQ ID NO: 23, SEQ ID NO: 31, SEQ ID NO: 39, SEQ ID NO: 47, SEQ ID NO: 55, SEQ ID NO: 63 and SEQ ID NO: 71.

Advantageously, in a preferred embodiment of the antibody according to the invention:

FR1 has at least 80% homology, preferably at least 90% homology, for example at least 95% homology, at least 96%, at least 97%, at least 98%, at least 99% or even 100% homology with SEQ ID NO: 5, FR2 has at least 80% homology, preferably at least 90% homology, for example at least 95% homology, at least 96%, at least 97%, at least 98%, at least 99% or even 100% homology with SEQ ID NO: 6, FR3 has at least 80% homology, preferably at least 90% homology, for example at least 95% homology, at least 96%, at least 97%, at least 98%, at least 99% or even 100% homology with SEQ ID NO: 7, and FR4 has at least 80% homology, preferably at least 90% homology, for example at least 95% homology, at least 96%, at least 97%, at least 98%, at least 99% or even 100% homology with SEQ ID NO: 8;

FR1 has at least 80% homology, preferably at least 90% homology, for example at least 95% homology, at least 96%, at least 97%, at least 98%, at least 99% or even 100% homology with SEQ ID NO: 12, FR2 has at least 80% homology, preferably at least 90% homology, for example at least 95% homology, at least 96%, at least 97%, at least 98%, at least 99% or even 100% homology with SEQ ID NO: 13, FR3, preferably at least 90% homology, for example at least 95% homology, at least 96%, at least 97%, at least 98%, at least 99% or even 100% homology has at least 80% homology with SEQ ID NO: 14, and FR4 has at least 80% homology, preferably at least 90% homology, for example at least 95% homology, at least 96%, at least 97%, at least 98%, at least 99% or even 100% homology with SEQ ID NO: 15;

FR1 has at least 80% homology, preferably at least 90% homology, for example at least 95% homology, at least 96%, at least 97%, at least 98%, at least 99% or even 100% homology with SEQ ID NO: 20, FR2 has at least 80% homology, preferably at least 90% homology, for example at least 95% homology, at least 96%, at least 97%, at least 98%, at least 99% or even 100% homology with SEQ ID NO: 21, FR3 has at least 80% homology, preferably at least 90% homology, for example at least 95% homology, at least 96%, at least 97%, at least 98%, at least 99% or even 100% homology with SEQ ID NO: 22, and FR4 has at least 80% homology, preferably at least 90% homology, for example at least 95% homology, at least 96%, at least 97%, at least 98%, at least 99% or even 100% homology with SEQ ID NO: 23;

FR1 has at least 80% homology, preferably at least 90% homology, for example at least 95% homology, at least 96%, at least 97%, at least 98%, at least 99% or even 100% homology with SEQ ID NO: 28, FR2 has at least 80% homology, preferably at least 90% homology, for example at least 95% homology, at least 96%, at least 97%, at least 98%, at least 99% or even 100% homology with SEQ ID NO: 29, FR3 has at least 80% homology, preferably at least 90% homology, for example at least 95% homology, at least 96%, at least 97%, at least 98%, at least 99% or even 100% homology with SEQ ID NO: 30, and FR4 has at least 80% homology, preferably at least 90% homology, for example at least 95% homology, at least 96%, at least 97%, at least 98%, at least 99% or even 100% homology with SEQ ID NO: 31;

FR1 has at least 80% homology, preferably at least 90% homology, for example at least 95% homology, at least 96%, at least 97%, at least 98%, at least 99% or even 100% homology with SEQ ID NO: 36, FR2 has at least 80% homology, preferably at least 90% homology, for example at least 95% homology, at least 96%, at least 97%, at least 98%, at least 99% or even 100% homology with SEQ ID NO: 37, FR3 has at least 80% homology, preferably at least 90% homology, for example at least 95% homology, at least 96%, at least 97%, at least 98%, at least 99% or even 100% homology with SEQ ID NO: 38, and FR4 has at least 80% homology, preferably at least 90% homology, for example at least 95% homology, at least 96%, at least 97%, at least 98%, at least 99% or even 100% homology with SEQ ID NO: 39;

FR1 has at least 80% homology, preferably at least 90% homology, for example at least 95% homology, at least 96%, at least 97%, at least 98%, at least 99% or even 100% homology with SEQ ID NO: 44, FR2 has at least 80% homology, preferably at least 90% homology, for example at least 95% homology, at least 96%, at least 97%, at least 98%, at least 99% or even 100% homology with SEQ ID NO: 45, FR3 has at least 80% homology, preferably at least 90% homology, for example at least 95% homology, at least 96%, at least 97%, at least 98%, at least 99% or even 100% homology with SEQ ID NO: 46, and FR4 has at least 80% homology, preferably at least 90% homology, for example at least 95% homology, at least 96%, at least 97%, at least 98%, at least 99% or even 100% homology with SEQ ID NO: 47;

FR1 has at least 80% homology, preferably at least 90% homology, for example at least 95% homology, at least 96%, at least 97%, at least 98%, at least 99% or even 100% homology with SEQ ID NO: 52, FR2 has at least 80% homology, preferably at least 90% homology, for example at least 95% homology, at least 96%, at least 97%, at least 98%, at least 99% or even 100% homology with SEQ ID NO: 53, FR3 has at least 80% homology, preferably at least 90% homology, for example at least 95% homology, at least 96%, at least 97%, at least 98%, at least 99% or even 100% homology with SEQ ID NO: 54, and FR4 has at least 80% homology, preferably at least 90% homology, for example at least 95% homology, at least 96%, at least 97%, at least 98%, at least 99% or even 100% homology with SEQ ID NO: 55;

FR1 has at least 80% homology, preferably at least 90% homology, for example at least 95% homology, at least 96%, at least 97%, at least 98%, at least 99% or even 100% homology with SEQ ID NO: 60, FR2 has at least 80% homology, preferably at least 90% homology, for example at least 95% homology, at least 96%, at least 97%, at least 98%, at least 99% or even 100% homology with SEQ ID NO: 61, FR3 has at least 80% homology, preferably at least 90% homology, for example at least 95% homology, at least 96%, at least 97%, at least 98%, at least 99% or even 100% homology with SEQ ID NO: 62, and FR4 has at least 80% homology, preferably at least 90% homology, for example at least 95% homology, at least 96%, at least 97%, at least 98%, at least 99% or even 100% homology with SEQ ID NO: 63; or FR1 has at least 80% homology, preferably at least 90% homology, for example at least 95% homology, at least 96%, at least 97%, at least 98%, at least 99% or even 100% homology with SEQ ID NO: 68, FR2 has at least 80% homology, preferably at least 90% homology, for example at least 95% homology, at least 96%, at least 97%, at least 98%, at least 99% or even 100% homology with SEQ ID NO: 69, FR3 has at least 80% homology, preferably at least 90% homology, for example at least 95% homology, at least 96%, at least 97%, at least 98%, at least 99% or even 100% homology with SEQ ID NO: 70, and FR4 has at least 80% homology, preferably at least 90% homology, for example at least 95% homology, at least 96%, at least 97%, at least 98%, at least 99% or even 100% homology with SEQ ID NO: 71.

In a particularly preferred embodiment of the antibody according to the invention, the amino acid sequence of formula (I) has at least 80% homology, preferably at least 90% homology, for example at least 95% homology, at least 96%, at least 97%, at least 98%, at least 99% or even 100% homology with an amino acid sequence chosen from SEQ ID NO: 4, SEQ ID NO: 16, SEQ ID NO: 24, SEQ ID NO: 32, SEQ ID NO: 40, SEQ ID NO: 48, SEQ ID NO: 56, SEQ ID NO: 64 and SEQ ID NO: 72.

The antibody according to the invention can bind to the G protein alpha in an isolated form and/or present in a membrane environment, for example it may bind to a G protein alpha present in a preparation of membranes bearing one or more GPCRs and one or more G proteins alpha.

Given that the antibody according to the invention binds to the protein, it is not necessary for the G protein alpha to be complexed with the GPCR for the antibody according to the invention to be able to bind to the G protein.

In a first particular embodiment, the antibody according to the invention has a better affinity for the full G protein alpha compared to the empty G protein alpha, in particular a better affinity for the G protein alpha bound to GTP gamma S. Thus, the "Kd for the empty G protein alpha/Kd for the full G protein alpha" ratio measured in FRET for the antibody of the invention is at least equal to 2, for example at least equal to 2.5, at least equal to 5, or at least equal to 10, and:
   CDR1 has at least 80% homology, preferably at least 90% homology, for example at least 95% homology, at least 96%, at least 97%, at least 98%, at least 99% or even 100% homology with one of the amino acid sequences chosen from SEQ ID NO: 1, SEQ ID NO: 9, SEQ ID NO: 17, SEQ ID NO: 25, SEQ ID NO: 33;
   CDR2 has at least 80% homology, preferably at least 90% homology, for example at least 95% homology, at least 96%, at least 97%, at least 98%, at least 99% or even 100% homology with the amino acid sequence SEQ ID NO: 2, SEQ ID NO: 10, SEQ ID NO: 18, SEQ ID NO: 26, SEQ ID NO: 34; and
   CDR3 has at least 80% homology, preferably at least 90% homology, for example at least 95% homology, at least 96%, at least 97%, at least 98%, at least 99% or even 100% homology with the amino acid sequence SEQ ID NO: 3, SEQ ID NO: 11, SEQ ID NO: 19, SEQ ID NO: 27, SEQ ID NO: 35.

In a second particular embodiment, the antibody according to the invention has a better affinity for the empty G protein alpha compared to the full G protein alpha. Thus, the "Kd for the full G protein alpha/Kd for the empty G protein alpha" ratio measured in FRET for the antibody of the invention is at least equal to 5, for example at least equal to 10, at least equal to 20, or at least equal to 50, and:
   CDR1 has at least 80% homology, preferably at least 90% homology, for example at least 95% homology, at least 96%, at least 97%, at least 98%, at least 99% or even 100% homology with one of the amino acid sequences chosen from SEQ ID NO: 41, SEQ ID NO: 49, SEQ ID NO: 57, SEQ ID NO: 65;
   CDR2 has at least 80% homology, preferably at least 90% homology, for example at least 95% homology, at least 96%, at least 97%, at least 98%, at least 99% or even 100% homology with the amino acid sequence SEQ ID NO: 42, SEQ ID NO: 50, SEQ ID NO: 58, SEQ ID NO: 66; and
   CDR3 has at least 80% homology, preferably at least 90% homology, for example at least 95% homology, at least 96%, at least 97%, at least 98%, at least 99% or even 100% homology with the amino acid sequence SEQ ID NO: 43, SEQ ID NO: 51, SEQ ID NO: 59, SEQ ID NO: 67.

The antibody according to the invention is particularly advantageous in performing a FRET assay, in particular for detecting a full G protein alpha or an empty G protein alpha. The antibody according to the invention may thus be coupled to a molecule enabling it to be detected. This may be a peptide tag, for example the tag 6×His. It may also be an enzyme capable of generating a signal detectable by colorimetry, fluorescence or luminescence when it is in the presence of its substrate, for example β-galactosidase, alkaline phosphatase or horseradish peroxidase. It may also be a radionuclide, a fluorescent compound, a luminescent compound or a dye. Advantageously, the antibody according to the invention is coupled to a member of a pair of FRET partners.

FRET Partner Pairs

The FRET partner pairs preferably consist of an energy donor fluorescent compound and an energy acceptor fluorescent compound.

FRET is defined as a non-radiative transfer of energy resulting from a dipole-dipole interaction between an energy donor and an energy acceptor. This physical phenomenon requires energy compatibility between these molecules. This means that the emission spectrum of the donor has to overlap, at least partially, the absorption spectrum of the acceptor. According to Förster's theory, FRET is a process which depends on the distance separating the two molecules, donor and acceptor: when these molecules are close to each other, and the donor compound is excited at a wavelength corresponding to one of its absorption peaks, there will be a transfer of energy, causing a reduction in the luminescence emitted at the emission wavelength of the donor, and an increase in the luminescence emitted at the emission wavelength of the acceptor.

The selection of the donor/acceptor fluorophore pair in order to obtain a FRET signal is within the abilities of those skilled in the art. Donor-acceptor pairs which can be used to study FRET phenomena are in particular described in the work of Joseph R. Lakowicz (Principles of fluorescence spectroscopy, 2nd edition, Kluwer Academic/Plenum Publishers, NY (1999)), to which those skilled in the art will be able to refer.

Energy donor fluorescent compounds having a long lifetime (>0.1 ms, preferably in the range 0.5-6 ms), in particular rare earth chelates or cryptates, are advantageous since they make it possible to perform time-resolved measurements, that is to say to measure TR-FRET signals while excluding the phenomenon of autofluorescence emitted by the measurement medium. For this reason and also generally, they are preferred for the implementation of the process according to the invention.

Complexes of dysprosium (Dy3+), of samarium (Sm3+), of neodymium (Nd3+), of ytterbium (Yb3+) or else of erbium (Er3+) are rare earth complexes which are also suitable for the purposes of the invention, but chelates and cryptates of europium (Eu3+) and of terbium (Tb3+) are particularly preferred.

A great number of rare earth complexes have been described and many are currently sold by the companies PerkinElmer, Invitrogen and Cisbio Bioassays.

Examples of rare earth chelates or cryptates which are suitable for the purposes of the invention are:

Lanthanide cryptates, comprising one or more pyridine units. Such rare earth cryptates are described for example in the patents EP 0 180 492, EP 0 321 353, EP 0 601 113 and in the international application WO 01/96 877. Cryptates of terbium (Tb3+) and of europium (Eu3+) are particularly suitable for the purposes of the present invention. Lanthanide cryptates are sold by the company Cisbio Bioassays. Mention may be made, by way of non-limiting example, of the europium cryptates of the formulae below (which may be coupled to the compound to be labeled via a reactive group, here for example an NH$_2$ group):

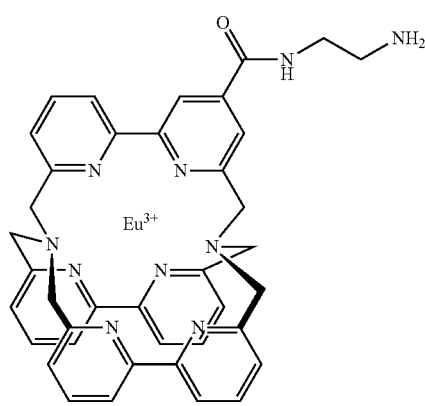

TrisBiPy-Eu

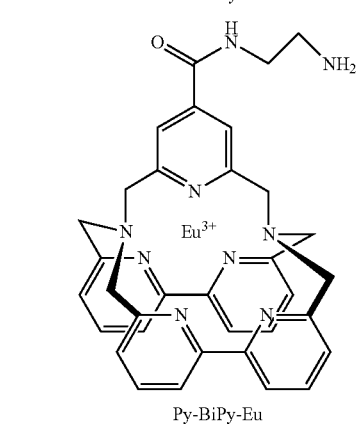

Py-BiPy-Eu

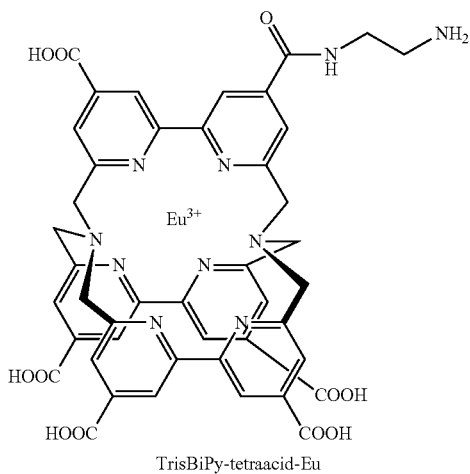

TrisBiPy-tetraacid-Eu

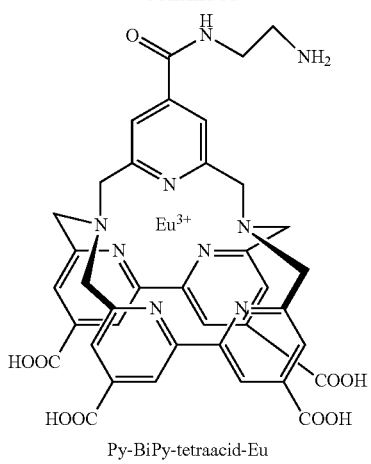

Py-BiPy-tetraacid-Eu

The lanthanide chelates described in particular in the patents U.S. Pat. Nos. 4,761,481, 5,032,677, 5,055,578, 5,106,957, 5,116,989, 4,761,481, 4,801,722, 4,794,191, 4,637,988, 4,670,572, 4,837,169, and 4,859,777. The patents EP 0 403 593, U.S. Pat. Nos. 5,324,825, 5,202,423, and 5,316,909 describe chelates composed of a nonadentate ligand such as terpyridine. Lanthanide chelates are sold by the company PerkinElmer.

Lanthanide complexes consisting of a chelating agent, such as tetraazacyclododecane, substituted by a chromophore comprising aromatic rings, such as those described by Poole R. et al. in Biomol. Chem, 2005, 3, 1013-1024 "Synthesis and characterisation of highly emissive and kinetically stable lanthanide complexes suitable for usage in cellulo", may also be used. It is also possible to use the complexes described in the application WO 2009/010580.

The lanthanide cryptates described in the patents EP 1 154 991 and EP 1 154 990 can also be used.

The terbium cryptate of the formula below (which may be coupled to a compound to be labeled via a reactive group, here for example an NH2 group):

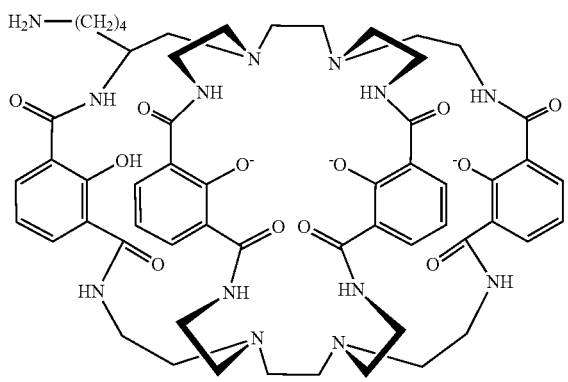

and the synthesis of which is described in the international application WO 2008/063721 (compound 6a on page 89).

The terbium cryptate Lumi4®-Tb from the company Lumiphore, sold by Cisbio Bioassays.

The quantum dye from the company Research Organics and having the formula below (which may be coupled to the compound to be labeled via a reactive group, here NCS):

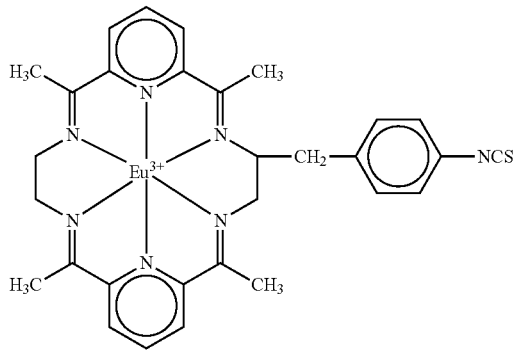

Ruthenium chelates, in particular complexes consisting of a ruthenium ion and a number of bipyridines, such as ruthenium(II) tris(2,2'-bipyridine).

The terbium chelate DTPA-cs124 Tb sold by the company Life Technologies and having the formula below (which may be coupled to the compound to be labeled via a reactive group R), the synthesis of which is described in the American patent U.S. Pat. No. 5,622,821.

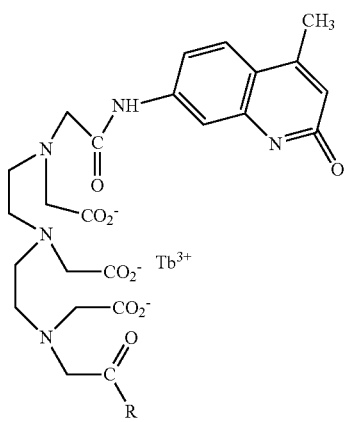

The terbium chelate of the formula below and described by Latva et al. (Journal of Luminescence 1997, 75: 149-169):

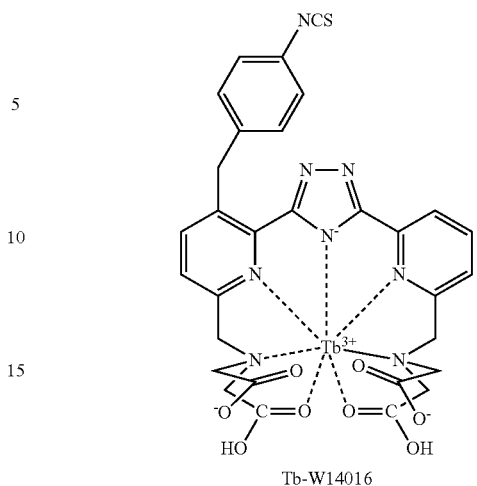

Tb-W14016

Particularly advantageously, the donor fluorescent compound is chosen from: a europium cryptate; a europium chelate; a terbium chelate; a terbium cryptate; a ruthenium chelate; and a quantum dye; chelates and cryptates of europium and of terbium being particularly preferred.

The acceptor fluorescent compound has to have an absorption spectrum which overlaps the emission spectrum of the donor (Mathis G, Clin. Chem. 1993, 39(9):1953-1959) and may be chosen from the following group: allophycocyanins, in particular those known under the trade name XL665; luminescent organic molecules such as rhodamines, cyanines (such as for example Cy5), squaraines, coumarins, proflavins, acridines, fluoresceins, boron-dipyrromethene derivatives (sold under the name "Bodipy"), the fluorophores known under the name "Atto", the fluorophores known under the name "DY", the compounds known under the name "Alexa", nitrobenzoxadiazole. Advantageously, the acceptor fluorescent compounds are chosen from allophycocyanins, rhodamines, cyanines, squaraines, coumarins, proflavins, acridines, fluoresceins, boron-dipyrromethene derivatives, nitrobenzoxadiazole.

The expressions "cyanines" and "rhodamines" should be understood to mean "cyanine derivatives" and "rhodamine derivatives", respectively. Those skilled in the art are aware of these various fluorophores, which are commercially available.

The "Alexa" compounds are sold by the company Invitrogen; the "Atto" compounds are sold by the company Atto-tec; the "DY" compounds are sold by the company Dyomics; the "Cy" compounds are sold by the company Amersham Biosciences; the other compounds are sold by various suppliers of chemical reagents such as the companies Sigma, Aldrich or Acros. For the purposes of the invention, derivatives of cyanines or fluorescein are preferred as acceptor fluorescent compounds.

Labeling of the Antibodies with Energy Acceptor or Donor Compounds

The antibodies according to the invention may be labeled with the fluorophores directly (covalently) or indirectly. Preferably, at least one of the FRET partners is covalently bonded to the first or to the second antibody, and even more preferably the two FRET partners are respectively covalently bonded to the first and to the second antibody.

The direct labeling of an antibody according to the invention with a fluorescent donor or acceptor compound is performed by conventional conjugation techniques involving the use of reactive groups. The fluorescent donor or acceptor compounds are generally sold in "functionalized" form, that is to say that they bear a reactive group capable of reacting with a functional group present on the compound to be labeled, in this case the antibody according to the invention.

Typically, the reactive group present on the donor or acceptor fluorescent compound is an electrophilic or nucleophilic group which can form a covalent bond when it is placed in the presence of an appropriate nucleophilic or electrophilic group, respectively. By way of examples, the electrophilic/nucleophilic group pairs and the type of covalent bond formed when they are brought together are listed below:

| Electrophilic group | Nucleophilic group | Type of bond |
|---|---|---|
| acrylamide | thiol | thioether |
| acyl halide | amine/aniline | carboxamide |
| aldehyde | amine/aniline | imine |
| aldehyde or ketone | hydrazine | hydrazone |
| aldehyde or ketone | hydroxylamine | oxime |
| alkyl sulfonate | thiol | thioether |
| anhydride | amine/aniline | carboxamide |
| aryl halide | thiol | thiophenol |
| aryl halide | amine | arylamine |
| aziridine | thiol | thioether |
| carbodiimide | carboxylic acid | N-acylurea or anhydride |
| activated ester* | amine/aniline | carboxamide |
| haloacetamide | thiol | thioether |
| halotriazine | amine/aniline | aminotriazine |
| imido ester | amine/aniline | amidine |
| isocyanate | amine/aniline | urea |
| isothiocyanate | amine/aniline | thiourea |
| maleimide | thiol | thioether |
| sulfonate ester | amine/aniline | alkylamine |
| sulfonyl halide | amine/aniline | sulfonamide |

*activated ester is understood to mean groups of the formula COY, where Y is:
a leaving group chosen from succinimidyloxy (—OCH$_4$NO$_2$) and sulfo-succinimidyloxy (—OC$_4$H$_3$NO$_2$—SO$_3$H) groups;
an aryloxy group which is unsubstituted or substituted by at least one electrophilic substituent such as nitro, fluoro, chloro, cyano and trifluoromethyl groups, thus forming an activated aryl ester;
a carboxylic acid activated by a carbodiimide group, forming an anhydride —OCORa or —OCNRaNHRb, in which Ra and Rb are identical or different and are chosen from C$_1$-C$_6$ alkyl, C$_1$-C$_6$ perfluoroalkyl, C1-C6 alkoxy and cyclohexyl groups; 3-dimethylaminopropyl, or N-morpholinoethyl.

The donor and acceptor fluorescent compounds commercially available generally include a maleimide function or an activated ester, most frequently an ester activated by an NHS (N-hydroxysuccinimidyl) group, which react with the thiol and amine groups respectively and can thus be used for the labeling of antibodies. The labeled antibodies are characterized by the final molar ratio (FMR), which represents the mean number of label molecules grafted to the antibody according to the invention.

It may be advantageous to use one of the functional groups naturally present in the antibody according to the invention: the terminal amino group, the terminal carboxylate group, the carboxylate groups of aspartic acid and glutamic acid, the amine groups of lysines, the guanidine groups of arginines, the thiol groups of cysteines, the phenol groups of tyrosines, the indole rings of tryptophans, the thioether groups of methionines, and the imidazole groups of histidines.

Another approach to labeling an antibody according to the invention with a fluorescent compound consists in introducing a reactive group into the antibody, for example an NHS group or a maleimide group, and placing it in the presence of a fluorophore bearing a functional group which will react with the reactive group to form a covalent bond.

It is important to verify that the labeled antibody according to the invention retains a sufficient affinity for the G protein alpha; this can be checked in a simple manner by conventional binding experiments which make it possible to calculate the affinity constant of the labeled antibody according to the invention for the G protein alpha.

The antibody according to the invention may also be labeled with a fluorescent compound indirectly, for example by introducing into the incubation medium a "secondary" antibody, itself covalently bonded to a fluorescent compound, this antibody specifically recognizing the antibody according to the invention or else a hapten present on this antibody according to the invention (such as a dinitrophenyl group, a dogoxigenin group, fluorescein, or FLAG, c-myc, or 6-HIS tags). The secondary antibody may be an anti-species antibody.

Another very conventional means for indirect labeling consists in attaching biotin to the antibody according to the invention to be labeled, and then incubating this biotinylated ligand in the presence of streptavidin labeled with a fluorophore. The labeling of the antibody according to the invention with biotin falls within the general knowledge of those skilled in the art, and the company Cisbio Bioassays sells for example streptavidin labeled with the fluorophore with the trade name "d2" (ref. 610SADLA).

TR-FRET Signal Measurement

The measurement of the TR-FRET signal is carried out after excitation of the measurement medium with a pulsed source in an excitation band of the donor compound, preferably after a delay of 1 to 500 microseconds (μs) and for a duration of 10 to 2000 μs. Even more preferably, the delay is 50 μs (time resolved).

The TR-FRET signal may consist of the intensity of the measured luminescence or of its lifetime.

The antibody according to the invention may be present in a polypeptide. It may also be immobilized on a solid support.

Another aspect of the invention relates to a complex comprising an antibody according to the invention, for example a complex comprising an antibody according to the invention and a G protein alpha.

The antibody according to the invention can be a "humanized" version, obtained for example by replacing one or more amino acids in the amino acid sequence of the antibody (and in particular in the FRs) with one or more amino acids appearing at the corresponding position(s) in a conventional human tetrameric antibody. Several humanization techniques are described in the literature and those skilled in the art will not have any difficulty in implementing them in order to prepare the antibodies according to the invention.

The antibody according to the invention can be produced by any technique known in the art, such as, without limitation, any chemical, biological, genetic or enzymatic technique alone or in combination.

When the amino acid sequence of the desired antibody is known, those skilled in the art can easily produce said antibody by conventional techniques for the production of polypeptides. For example, the antibody according to the invention can be synthesized using a well-known solid-phase method, preferably using a commercially available polypeptide synthesis apparatus (such as that manufactured by Applied Biosystems, Foster City, Calif.) and following the manufacturer's instructions. As a variant, the antibody according to the invention can be synthesized by recombinant DNA techniques known in the literature. For example, the antibody according to the invention can be obtained by expressing a nucleic acid sequence coding for said antibody after incorporation of said nucleic sequence into one or more expression vectors and introduction of such vectors into an appropriate host cell which will express the desired antibody.

Advantageously, the antibody according to the invention is purified (or isolated), for example from the culture supernatant of host cells expressing the desired antibody, by performing known purification techniques, such as purification on chromatography and/or affinity columns.

Other Subjects

A third subject of the present invention relates to a nucleic acid sequence coding for an antibody according to the invention.

A fourth subject of the present invention relates to a recombinant vector comprising a nucleic acid sequence according to the invention. Any type of vector suitable for the production of antibodies can be used in the context of the invention. The vector will comprise the nucleic sequences necessary to produce the antibody according to the invention, for example promoter sequences, regulatory sequences, etc. The preparation of an appropriate vector is widely described in the literature.

A fifth subject of the invention relates to a cell comprising a vector according to the invention or a nucleic acid sequence according to the invention. The cell according to the invention may be obtained by methods which are widely described in the literature, for example by transfecting a cell clone with a vector according to the invention or a nucleic acid sequence.

The invention is not restricted to a particular cell type. Any cell capable of producing antibodies can be used in the context of the invention. They may be eukaryotic cells, such as mammalian cells, for example human or mouse cells, or prokaryotic cells, for example bacteria, or else yeasts.

The invention will be further illustrated by the figures and examples which follow. However, these examples and these figures should not in any way be interpreted as limiting the scope of the invention.

SEQUENCE LISTING

| Name | SEQ ID NO: | SEQUENCE |
|---|---|---|
| F11 CDR1 | 1 | GFAFSDTW (SEQ ID NO: 1) |
| F11 CDR2 | 2 | ITRGDQNT (SEQ ID NO: 2) |
| F11 CDR3 | 3 | AKEGPIGPPDY (SEQ ID NO: 3) |
| F11 FR1 | 5 | EVQLVESGGGLVQPGGSLRLSCEAS (SEQ ID NO: 5) |
| F11 FR2 | 6 | MYWVRQAPGKGLEWVAT (SEQ ID NO: 6) |
| F11 FR3 | 7 | YYTESVKGRFTISRDNAKNTLYLQMNSLKSEDTAVYYC (SEQ ID NO: 7) |
| F11 FR4 | 8 | WGQGTQVTVSSAAAEQKLISEEDLNGAAHHHHHHGS (SEQ ID NO: 8) |
| F11 | 4 | EVQLVESGGGLVQPGGSLRLSCEASGFAFSDTWMYWVRQAPGKGLEWVATIT RGDQNTYYTESVKGRFTISRDNAKNTLYLQMNSLKSEDTAVYYCAKEGPIGPP DYWGQGTQVTVSSAAAEQKLISEEDLNGAAHHHHHHGS (SEQ ID NO: 4) |
| B11 CDR1 | 9 | GFTFNDYW (SEQ ID NO: 9) |
| B11 CDR2 | 10 | INTGGSST (SEQ ID NO: 10) |
| B11 CDR3 | 11 | AKEGPVGPPDY (SEQ ID NO: 11) |
| B11 FR1 | 12 | EVQLVESGGGLVQPGGSLRLSCAAS (SEQ ID NO: 12) |
| B11 FR2 | 13 | MYWVRQAPGKGLEWVSS (SEQ ID NO: 13) |
| B11 FR3 | 14 | YYSDSVKGRFTTARDNAKNSLYLQLNSLRPEDTAVYYC (SEQ ID NO: 14) |
| B11 FR4 | 15 | WGQGTQVTVSSAAAEQKLISEEDLNGAAHHHHHHGS (SEQ ID NO: 15) |
| B11 | 16 | EVQLVESGGGLVQPGGSLRLSCAASGFTFNDYWMYWVRQAPGKGLEWVSSIN TGGSSTYYSDSVKGRFTTARDNAKNSLYLQLNSLRPEDTAVYYCAKEGPVGPP DYWGQGTQVTVSSAAAEQKLISEEDLNGAAHHHHHHGS (SEQ ID NO: 16) |
| F9 CDR1 | 17 | GFTFDDYA (SEQ ID NO: 17) |
| F9 CDR2 | 18 | ISSRGITT (SEQ ID NO: 18) |
| F9 CDR3 | 19 | ATDPSTWYRGTAH (SEQ ID NO: 19) |
| F9 FR1 | 20 | EVQLVESGGGLVQPGGSLRLSCAAS (SEQ ID NO: 20) |
| F9 FR2 | 21 | MNWVRQAAGKGPEWVAS (SEQ ID NO: 21) |
| F9 FR3 | 22 | DYAHSVKGRFTVSRDNTKNTLYLQMNSLKPDDAAVYYC (SEQ ID NO: 22) |
| F9 FR4 | 23 | WGQGTQVTVSSAAAEQKLISEEDLNGAAHHHHHHGS (SEQ ID NO: 23) |
| F9 | 24 | EVQLVESGGGLVQPGGSLRLSCAASGFTFDDYAMNWVRQAAGKGPEWVASIS SRGITTDYAHSVKGRFTVSRDNTKNTLYLQMNSLKPDDAAVYYCATDPSTWY |

-continued

| Name | SEQ ID NO: | SEQUENCE |
|---|---|---|
| | | RGTAHWGQGTQVTVSSAAAEQKLISEEDLNGAAHHHHHHGS (SEQ ID NO: 24) |
| G6 CDR1 | 25 | GFTFSTYR (SEQ ID NO: 25) |
| G6 CDR2 | 26 | ISSRGITT (SEQ ID NO: 26) |
| G6 CDR3 | 27 | ATDPSTWYRGTAH (SEQ ID NO: 27) |
| G6 FR1 | 28 | EVQLVESGGDLVQPGGSLRLSCAAS (SEQ ID NO: 28) |
| G6 FR2 | 29 | MNWVRQAPGKGLEWVAS (SEQ ID NO: 29) |
| G6 FR3 | 30 | DYAHPVKGRFTVSRDNTKNTLYLQMNSLKPDDAAVYYC (SEQ ID NO: 30) |
| G6 FR4 | 31 | WGQGTQVTVSSAAAEQKLISEEDLNGAAHHHHHHGS (SEQ ID NO: 31) |
| G6 | 32 | EVQLVESGGDLVQPGGSLRLSCAASGFTFSTYRMNWVRQAPGKGLEWVASIS SRGITTDYAHPVKGRFTVSRDNTKNTLYLQMNSLKPDDAAVYYCATDPSTWY RGTAHWGQGTQVTVSSAAAEQKLISEEDLNGAAHHHHHHGS (SEQ ID NO: 32) |
| F4 CDR1 | 33 | GFTFSSYY (SEQ ID NO: 33) |
| F4 CDR2 | 34 | TYNGDGDT (SEQ ID NO: 34) |
| F4 CDR3 | 35 | NAYDGTLLRDY (SEQ ID NO: 35) |
| F4 FR1 | 36 | EVQLVESGGGLVQPGGSLRLSCAAS (SEQ ID NO: 36) |
| F4 FR2 | 37 | MNWVRQAPGKGLEWVSS (SEQ ID NO: 37) |
| F4 FR3 | 38 | DYSDSVKGRFTISRDNAKNTVYLEMSDLKVQDTAIYYC (SEQ ID NO: 38) |
| F4 FR4 | 39 | WGQGTQVTVSSAAAEQKLISEEDLNGAAHHHHHHGS (SEQ ID NO: 39) |
| F4 | 40 | EVQLVESGGGLVQPGGSLRLSCAASGFTFSSYYMNWVRQAPGKGLEWVSSIY NGDGDTDYSDSVKGRFTISRDNAKNTVYLEMSDLKVQDTAIYYCNAYDGTLLR DYWGQGTQVTVSSAAAEQKLISEEDLNGAAHHHHHHGS (SEQ ID NO: 40) |
| A10 CDR1 | 41 | GLTYSDYA (SEQ ID NO: 41) |
| A10 CDR2 | 42 | ISSRGITT (SEQ ID NO: 42) |
| A10 CDR3 | 43 | TTVSYWRYEY (SEQ ID NO: 43) |
| A10 FR1 | 44 | EVQLVESGGGLVQPGGSLRLSCAAS (SEQ ID NO: 44) |
| A10 FR2 | 45 | MSWVRQAAGKGPEWVAS (SEQ ID NO: 45) |
| A10 FR3 | 46 | DYAHSVKGRFTVSRDNTKNTLYLQMNSLEPEDTAVYYC (SEQ ID NO: 46) |
| A10 FR4 | 47 | WGQGTQVTVSSAAAEQKLISEEDLNGAAHHHHHHGS (SEQ ID NO: 47) |
| A10 | 48 | EVQLVESGGGLVQPGGSLRLSCAASGLTYSDYAMSWVRQAAGKGPEWVASIS SRGITTDYAHSVKGRFTVSRDNTKNTLYLQMNSLEPEDTAVYYCTTVSYWRYE YWGQGTQVTVSSAAAEQKLISEEDLNGAAHHHHHHGS (SEQ ID NO: 48) |
| F2 CDR1 | 49 | GFTFSSYA (SEQ ID NO: 49) |
| F2 CDR2 | 50 | ISSRGITT (SEQ ID NO: 50) |
| F2 CDR3 | 51 | VKGWMPTG (SEQ ID NO: 51) |
| F2 FR1 | 52 | EVQLVESGGGLVQPGGSLRLSCAAS (SEQ ID NO: 52) |
| F2 FR2 | 53 | MSWVRQAAGKGPEWVAS (SEQ ID NO: 53) |
| F2 FR3 | 54 | DYAHSVKGRFTVSRDNTKNTLYLQMNSLKPEDTALYYC (SEQ ID NO: 54) |
| F2 FR4 | 55 | WGQGTQVTVSSAAAEQKLISEEDLNGAAHHHHHHGS (SEQ ID NO: 55) |

SEQUENCE LISTING

| Name | SEQ ID NO: | SEQUENCE |
|---|---|---|
| F2 | 56 | EVQLVESGGGLVQPGGSLRLSCAASGFTFSSYAMSWVRQAAGKGPEWVASIS SRGITTDYAHSVKGRFTVSRDNTKNTLYLQMNSLKPEDTALYYCVKGWMPTG WGQGTQVTVSSAAAEQKLISEEDLNGAAHHHHHHGS (SEQ ID NO: 56) |
| E2 CDR1 | 57 | GYTFSSYA (SEQ ID NO: 57) |
| E2 CDR2 | 58 | ISSRGITT (SEQ ID NO: 58) |
| E2 CDR3 | 59 | TRVLWYENGLYSLNDF (SEQ ID NO: 59) |
| E2 FR1 | 60 | EVQLVESGGGLVQPGGSLRLSCIGS (SEQ ID NO: 60) |
| E2 FR2 | 61 | MAWVRQASGKGPEWVAS (SEQ ID NO: 61) |
| E2 FR3 | 62 | DYAHSVKGRFTISRDNAKNTLYLHMNNLKPEDTALYYC (SEQ ID NO: 62) |
| E2 FR4 | 63 | WGQGTQVTVSSAAAEQKLISEEDLNGAAHHHHHHGS (SEQ ID NO: 63) |
| E2 | 64 | EVQLVESGGGLVQPGGSLRLSCIGSGYTFSSYAMAWVRQASGKGPEWVASISS RGITTDYAHSVKGRFTISRDNAKNTLYLHMNNLKPEDTALYYCTRVLWYENGL YSLNDFWGQGTQVTVSSAAAEQKLISEEDLNGAAHHHHHHGS (SEQ ID NO: 64) |
| G7 CDR1 | 65 | GFTFSWYG (SEQ ID NO: 65) |
| G7 CDR2 | 66 | ISSRGITT (SEQ ID NO: 66) |
| G7 CDR3 | 67 | TRVLWYDSGAYSLNDF (SEQ ID NO: 67) |
| G7 FR1 | 68 | QVQLQESGGGLVQPGGSLRLSCAAS (SEQ ID NO: 68) |
| G7 FR2 | 69 | MSWVRQAPGKGPEWVAS (SEQ ID NO: 69) |
| G7 FR3 | 70 | DYAHSVKGRFTVSRDNTKNTLYLQMNSLKPEDTGVYYC (SEQ ID NO: 70) |
| G7 FR4 | 71 | WGQGTQVTVSSAAAEQKLISEEDLNGAAHHHHHHGS (SEQ ID NO: 71) |
| G7 | 72 | QVQLQESGGGLVQPGGSLRLSCAASGFTFSWYGMSWVRQAPGKGPEWVASI SSRGITTDYAHSVKGRFTVSRDNTKNTLYLQMNSLKPEDTGVYYCTRVLWYDS GAYSLNDFWGQGTQVTVSSAAAEQKLISEEDLNGAAHHHHHHGS (SEQ ID NO: 72) |

EXAMPLES

Example 1: Immunization of Llamas and Construction of an sdAb Library

Two llamas (*Lama glama*) were immunized subcutaneously with the recombinant human protein TST-Galphai1 (Galphai1 protein with UniProt sequence P63096-1, tagged at the N-terminus with the TwinStreptag (TST) (IBA) tag via a TEV linker) bound to GDP or to GTPgS. The construction of a VH/$V_HH$ library was carried out in the *E. coli* strain TG1 as described previously in (Alvarez-Rueda, Behar et al., 2007, Behar Chames et al. 2009). The diversity of the libraries obtained was greater than $10^8$ clones.

Production of Phage-VH/$V_HH$ Particles

Fifty ml of 2YTA (2YT containing 100 μg/ml of ampicillin) were inoculated with 50 μl of the bacteria library and incubated at 37° C. with shaking (250 rpm) to an $OD_{600}$ of between 0.4 and 0.6. The bacteria were infected with the phage KM13 using a multiplicity of infection of 20, for 30 min at 37° C. without shaking. The culture was centrifuged for 10 minutes at 3000 g, and the bacterial pellet was resuspended in 250 ml of 2YTA containing 50 μg/ml of kanamycin in order to produce VH-phages overnight at 30° C. with shaking. The culture was divided into 10 tubes and centrifuged for 20 minutes at 3000 g and 4° C. For each tube, 5 ml of 20% PEG 8000, 2.5 mM NaCl were added to the supernatant in a new, clean tube and incubated for 1 h on ice in order to induce the precipitation of the phage particles. The solution was centrifuged for 15 min at 3000 g and 4° C. and the pellet containing the phages was resuspended in 1 ml of PBS. Another centrifugation step (2 min, 16 000 g) was performed to remove bacterial contaminants and 200 μl of PEG 8000 NaCl were added to the supernatants in a new tube. After 30 min on ice and a final centrifugation (5 min, 16 000 g), the pellet containing the phage was resuspended in 1 ml of PBS to obtain a phage-VH ready to use for the selections.

Selection of VH/$V_HH$ by Phage Display

After a step of depletion of the phage library on a plate containing immobilized Strep-Tactin (IBA #2-4101-001) to avoid selection of anti-Strep-Tactin VH, a first selection cycle was carried out on a Strep-Tactin plate containing recombinant human Galphai1 fused to a Twin-Strep-tag and preloaded with 10 μM GDP for 2 h at 37° C. and saturated with 2% BSA in PBS for 1 h at room temperature. After 2 hours of incubation at room temperature, the plates were washed with 0.1% Tween PBS and PBS. Bound phages were eluted using a 1 mg/ml trypsin solution (Sigma) for 30 minutes at room temperature with shaking. The phages were recovered and amplified by infection of the TG1 bacterial strain. A second selection cycle was carried out in a similar manner on Galphai1 preloaded with 10 μM GTP. A second strategy consisted in two rounds of selection against Galphai1 in the absence of nucleotides. A third strategy aiming to promote the selection of VHs specific for the active conformation (GTP) of Galphai consisted in two selection cycles on Galphai1 Twin-Strep-tag preloaded with 10 μM GTPgS, followed by a depletion step performed on a plate coated with Galphai1 Twin-Strep-tag preloaded with 10 μM GDP. Individual TG1 colonies were cultured in 96-well deep well plates in 400 μl of 2YTA containing 2% glucose. After overnight growth, the culture was frozen at −80° C. in 20% glycerol and the remainder of the culture was used for the production of soluble VH induced by isopropyl-β-D-thiogalactopyranoside (IPTG) in 2YTA. The supernatants containing the VHs were used for the screening assays.

Production and Purification of VH

For the large-scale VH production, positive phagemids were transformed into the *E. coli* strain BL21 DE3. The transformed bacteria were cultured in 400 ml of 2YTA to an $OD_{600}$ value of 0.7 and induced with 100 μM IPTG for overnight growth at 30° C. with shaking. The bacteria were recovered by centrifugation and lysed using Bugbuster™ reagent (Novagen). After centrifugation for 20 minutes at 3000 g, the VHs were purified from the supernatant using TALON® Superflow™ (GE Healthcare) affinity chromatography according to the manufacturer's instructions.

Production of the VH-HcAbs

The VH genes were cloned into the pHLsec vector (Aricescu A R, Lu W, Jones E Y. Acta Crystallogr D Biol Crystallogr. 2006 October; 62(Pt 10):1243-50) by fusion with the gene coding for the CH2 and CH3 domains of a human IgG1, followed by a 6histidines tag, via gene synthesis (Genecust). The corresponding plasmid was used to transfect the suspension-adapted HEK293 line, and the cells were incubated with stirring according to the manufacturer's instructions (FreeStyle 293 Expression System, Thermofisher). After 5 days, the supernatants were recovered and used directly to purify the HcAbs by TALON® Superflow™ affinity chromatography according to the manufacturer's instructions.

Example 2: Determination of the Affinity Constant (Kd) of Single-Domain Antibodies (sdAbs) According to the Invention in FRET (HTRF)

Materials:

The recombinant TST-Galphai1 protein (Galphai1 protein with UniProt sequence P63096-1 tagged at the N-terminus with the TwinStreptag tag (TST) (IBA) via a TEV linker) was produced in Sf9 insect cells (infection via Baculovirus) and then purified on an affinity column via the TwinStreptag (TST) tag (Strep-Tactin Superflow high-capacity resin (IBA, catalog: 2-1208-002)).

An anti-TST antibody (anti-Twin-Strep-Tag, catalog reference 2-1517-001 from IBA) was labeled with the Lumi4®-Tb donor fluorescent probe, compatible for TR-FRET detection with the acceptor d2. The antibody thus obtained was called "anti-TST antibody-Lumi4®-Tb".

For the large-scale production of the nine heavy chain variable domains (VH) (F9: SEQ ID No: 24, F4: SEQ ID No: 40, B11: SEQ ID No: 16, F11: SEQ ID No: 4, G6: SEQ ID No: 32, A10: SEQ ID No: 48, E2: SEQ ID No: 64, F2: SEQ ID No: 56 and G7: SEQ ID No: 72), phagemids coding said VHs were transformed into the *E. coli* strain BL21 DE3. The transformed bacteria were cultured in 400 ml of 2YTA to an $OD_{600}$ value of 0.7 and induced with 100 μM IPTG for overnight growth at 30° C. with stirring. The bacteria were recovered by centrifugation and lysed using Bugbuster™ reagent (Novagen). After centrifugation for 20 minutes at 3000 g, the VHs were purified from the supernatant using TALON® Superflow™ (GE Healthcare) affinity chromatography according to the manufacturer's instructions.

For the production of the VH-type heavy-chain antibodies (VH-HcAbs), the VH genes were cloned into the pHLsec vector (Aricescu A R, Lu W, Jones E Y. Acta Crystallogr D Biol Crystallogr. 2006 October; 62(Pt 10):1243-50) by fusion with the gene coding for the CH2 and CH3 domains of a human IgG1, followed by a 6histidines tag, via gene synthesis (Genecust). The corresponding plasmid was used to transfect the suspension-adapted HEK293 line, and the cells were incubated with shaking according to the manufacturer's instructions (FreeStyle 293 Expression System, Thermofisher). After 5 days, the supernatants were recovered and used directly for purifying the VH-HcAbs by TALON® Superflow™ affinity chromatography according to the manufacturer's instructions.

The sdAbs obtained (VH or VH-HcAb) were labeled with the acceptor fluorescent probe d2, compatible for TR-FRET detection with the donor Lumi4®-Tb which was used to label the anti-TST antibody. The labeled antibodies were called "anti-Galphai antibody-d2".

The GDP and GTPγS nucleotides were purchased from Sigma Aldrich (respective catalog references G7127 and G8634).

The white, 384-low-volume-well, white-bottomed plates were purchased from Greiner Bio One (catalog reference 784075).

Method:

1) Preparation of the Reagents:

All the reagents were diluted in 50 mM Tris-HCl buffer pH 7.4, 10 mM $MgCl_2$, 10 mM NaCl, 0.1% BSA. The recombinant TST-Galphai1 protein was prepared 4× for use at 1 nM final concentration in the well (unless specified otherwise). The GDP or GTPγS nucleotides were prepared 4× for use at 10 μM final concentration in the well. The anti-TST antibody-Lumi4®-Tb was prepared 4× for use at 0.25 nM final concentration in the well. The anti-Galphai-d2 antibodies were prepared 4× to aim for the final concentrations in the wells indicated in the graphs, ranging up to 200 nM.

2) Distribution of the Reagents in the 384-Well Plates:
 TST-Galphai1 protein: 5 μl
 Nucleotides (GDP or GTPgS): 5 μl
 anti-TST antibody-Lumi4®-Tb (donor): 5 μl
 anti-Galphai antibody-d2 (acceptor): 5 μl The nonspecific signal (fluorescence background noise) was measured with wells containing only the two detection reagents (labeled with the donor and acceptor), that is to say the anti-TST antibody-Lumi4®-Tb (donor) and the anti-Galphai antibody-d2 (acceptor), the other components having been replaced by their dilution buffer.

3) Reading the HTRF Signal:

The plates were incubated at 21° C. for 20 h and then the HTRF signal was measured on a PHERAstar reader from BMG Labtech, with the following configuration:
 Module: HTRF (excitation 337 nm, emission 665 nm and 620 nm)
 Excitation: laser, 40 flashes
 Reading window: delays: 60 μs—integration: 400 μs 4) Signal Processing:

The HTRF ratio was calculated from the raw signals at 665 nm and 620 nm according to the following formula:

HTRF ratio=signal at 665 nm/signal at 620 nm*10 000

5) Principle of the TR-FRET (HTRF) Assay for the Determination of the Affinity (Kd) of the Heavy Chain Variable Domains VH The TR-FRET (HTRF) test made it possible to determine the affinity (Kd) of the various antibodies for the Galphai1 protein; FIG. 2 illustrates the principle of this test. A fixed concentration (1 nM) of the recombinant Galphai1 protein purified and tagged with TST (TST-Galphai1 protein) was placed in the presence of an excess of nucleotide (GDP or GTPgS) (10 μM), of a fixed concentration (0.5 nM) of anti-TST antibody labeled with the donor Lumi4®-Tb (anti-TST antibody-Lumi4®-Tb) and of increasing concentrations of VH-type single-domain antibodies labeled with the acceptor d2 (anti-Galphai VH antibody-d2). The total HTRF signal was then obtained.

In parallel, a condition without Galphai1 protein was carried out in order to determine the nonspecific HTRF signal.

The specific HTRF signal of the interaction between the antibody and the Galphai1 protein was then calculated by subtracting the nonspecific signal from the total signal. The data of the specific HTRF signal were then analyzed on GraphPad Prism7 software using a "one site specific binding" fit. The dissociation constant (Kd) of the antibody for the Galphai1 protein was then determined. The results which were obtained with the antibodies which bind to the G protein alpha bound to GTP gamma S and with the antibodies which bind to the G protein alpha bound to GDP are shown in Tables 1 and 2 below.

6) Principle of the HTRF (TR-FRET) Assay for the Determination of the Affinity (Kd) of the VH-Type Heavy-Chain Antibodies (VH HcAbs)

FIG. 12 illustrates the principle of the TR-FRET (HTRF) assay which was carried out to determine the affinity (Kd) of the various VH-HcAbs for the Galphai1 protein. A fixed concentration (1 nM) of the recombinant Galphai1 protein purified and tagged with TST (TST-Galphai1 protein) is placed in the presence of an excess of nucleotide (GDP or GTPgS) (10 μM), of a fixed concentration (0.5 nM) of anti-TST antibody labeled with the donor Lumi4®-Tb (anti-Tag Ab-Donor), of a fixed concentration (50 nM) of anti-6HIS antibody labeled with the acceptor d2 (anti-6HIS-acceptor antibody, Cisbio Bioassays #61HISDLF), and of increasing concentrations of a VH-HcAb antibody tagged with 6HIS (6HIS-Fc-sdAb). The total HTRF signal was then obtained.

In parallel, a condition without Galphai1 protein is carried out in order to determine the nonspecific HTRF signal.

The specific HTRF signal of the interaction between the VH-HcAb and the Galphai1 protein was then calculated by subtracting the nonspecific signal from the total signal. The data of the specific HTRF signal were then analyzed on GraphPad Prism7 software using a "one site specific binding" fit. The dissociation constant (Kd) of the VH-HcAb for the Galphai1 protein was then determined. The results obtained with the antibodies HcAb-B11, HcAb-F9, HcAb-G7, HcAb-A10 are shown in Table 3 below.

Results:

FIGS. 3 to 11 show the saturation curves obtained for the VHs.

The VHs (F9, F11, B11, F4 and G6) have an increased affinity for the G protein alpha bound to GTP gamma S, with a dissociation constant (Kd) of less than 100 nM ranging down to 1 nM for example for the antibody B11.

TABLE 1

Affinity (Kd in nM) of the VHs for the G alphai1 protein bound to GTPgammaS and for the empty G alphai1 protein

| Antibody tested | Affinity (mean Kd in nM) for the G protein alpha bound to GTPgS | Affinity (mean Kd in nM) for the empty G protein alpha |
| --- | --- | --- |
| F9 | 32 nM | >200 nM |
| F11 | 3 nM | 17 nM |
| B11 | 1 nM | 17 nM |
| F4 | 31 nM | 83 nM |
| G6 | 95 nM | >150 nM |

The VHs (A10, G7, F2 and E2) have an increased affinity for the G protein alpha bound to GDP, with a dissociation constant (Kd) of less than 100 nM ranging down to 14 nM for example for the antibody F2.

TABLE 2

Affinity (Kd in nM) of the VHs for the G alphai1 protein bound to GDP and for the empty G alphai1 protein

| Antibody tested | Affinity (mean Kd in nM) for the G protein alpha bound to GDP | Affinity (mean Kd in nM) for the empty G protein alpha |
| --- | --- | --- |
| A10 | 15 nM | 1 nM |
| G7 | 31 nM | 5 nM |
| F2 | 14 nM | 1 nM |
| E2 | 72 nM | 2 nM |

FIGS. 13 to 16 show the saturation curves obtained for the VH HcAbs.

The antibodies HcAb-B11, HcAb-F9, HcAb-G7 and HcAb-A10 have an increased affinity for the G protein alpha bound to GDP or to GTP gamma S, with a dissociation constant (Kd) of less than 10 nM ranging down to 1 nM for example for the antibody HcAb-B11 which binds to the G protein alpha bound to GTP gamma S.

TABLE 3

Affinity (Kd in nM) of the VH-HcAbs for the G alphai1 protein bound to GDP or to GTPgammaS

| Antibody tested | Affinity (mean Kd in nM) for the full G protein alpha bound to GDP or GTPgammaS) |
| --- | --- |
| HcAb-B11 | 1 nM for GTPgammaS |
| HcAb-F9 | 3 nM for GTPgammaS |
| HcAb-G7 | 5 nM for GDP |
| HcAb-A10 | 3 nM for GDP |

The invention claimed is:

1. A single-domain antibody (sdAb) which binds to G protein alpha, comprising an amino acid sequence consisting of 3 CDR regions (CDR1 to CDR3) and 4 hinge regions (FR1 to FR4) according to the following formula (I):

FR1-CDR1-FR2-CDR2-FR3-CDR3-FR4    (I)

said antibody having a dissociation constant (Kd) for the full G protein alpha, measured in Fluorescence Resonance Energy Transfer (FRET), of less than 100 nM, and wherein:
   CDR1 comprises the amino acid sequence of SEQ ID NO: 1, CDR2 comprises the amino acid sequence of SEQ ID NO: 2 and CDR3 comprises the amino acid sequence of SEQ ID NO: 3;
   CDR1 comprises the amino acid sequence of SEQ ID NO: 9, CDR2 comprises the amino acid sequence of SEQ ID NO: 10 and CDR3 comprises the amino acid sequence of SEQ ID NO: 11;
   CDR1 comprises the amino acid sequence of SEQ ID NO: 17, CDR2 comprises the amino acid sequence of SEQ ID NO: 18 and CDR3 comprises the amino acid sequence of SEQ ID NO: 19;
   CDR1 comprises the amino acid sequence of SEQ ID NO: 25, CDR2 comprises the amino acid sequence of SEQ ID NO: 26 and CDR3 comprises the amino acid sequence of SEQ ID NO: 27;
   CDR1 comprises the amino acid sequence of SEQ ID NO: 33, CDR2 comprises the amino acid sequence of SEQ ID NO: 34 and CDR3 comprises the amino acid sequence of SEQ ID NO: 35;
   CDR1 comprises the amino acid sequence of SEQ ID NO: 41, CDR2 comprises the amino acid sequence of SEQ ID NO: 42 and CDR3 comprises the amino acid sequence of SEQ ID NO: 43;
   CDR1 comprises the amino acid sequence of SEQ ID NO: 49, CDR2 comprises the amino acid sequence of SEQ ID NO: 50 and CDR3 comprises the amino acid sequence of SEQ ID NO: 51;
   CDR1 comprises the amino acid sequence of SEQ ID NO: 57, CDR2 comprises the amino acid sequence of SEQ ID NO: 58 and CDR3 comprises the amino acid sequence of SEQ ID NO: 59; or
   CDR1 comprises the amino acid sequence of SEQ ID NO: 65, CDR2 comprises the amino acid sequence of SEQ ID NO: 66 and CDR3 comprises the amino acid sequence of SEQ ID NO: 67.

2. The antibody as claimed in claim 1, wherein:

FR1 comprises an amino acid sequence selected from the group consisting of SEQ ID NO: 5, SEQ ID NO: 12, SEQ ID NO: 20, SEQ ID NO: 28, SEQ ID NO: 36, SEQ ID NO: 44, SEQ ID NO: 52, SEQ ID NO: 60 and SEQ ID NO: 68;

FR2 comprises an amino acid sequence selected from the group consisting of SEQ ID NO: 6, SEQ ID NO: 13, SEQ ID NO: 21, SEQ ID NO: 29, SEQ ID NO: 37, SEQ ID NO: 45, SEQ ID NO: 53, SEQ ID NO: 61 and SEQ ID NO: 69; and FR3 comprises an amino acid sequence selected from the group consisting of SEQ ID NO: 7, SEQ ID NO: 14, SEQ ID NO: 22, SEQ ID NO: 30, SEQ ID NO: 38, SEQ ID NO: 46, SEQ ID NO: 54, SEQ ID NO: 62 and SEQ ID NO: 70; and FR4 comprises an amino acid sequence selected from the group consisting of SEQ ID NO: 8, SEQ ID NO: 15, SEQ ID NO: 23, SEQ ID NO: 31, SEQ ID NO: 39, SEQ ID NO: 47, SEQ ID NO: 55, SEQ ID NO: 63 and SEQ ID NO: 71.

3. The antibody as claimed in claim 1, wherein:

FR1 comprises SEQ ID NO: 5, FR2 comprises SEQ ID NO: 6 and FR3 comprises SEQ ID NO: 7;

FR1 comprises SEQ ID NO: 12, FR2 comprises SEQ ID NO: 13 and FR3 comprises SEQ ID NO: 14;

FR1 comprises SEQ ID NO: 20, FR2 comprises SEQ ID NO: 21 and FR3 comprises SEQ ID NO: 22;

FR1 comprises SEQ ID NO: 28, FR2 comprises SEQ ID NO: 29 and FR3 comprises SEQ ID NO: 30;

FR1 comprises SEQ ID NO: 36, FR2 comprises SEQ ID NO: 37 and FR3 comprises SEQ ID NO: 38;

FR1 comprises SEQ ID NO: 44, FR2 comprises SEQ ID NO: 45 and FR3 comprises SEQ ID NO: 46;

FR1 comprises SEQ ID NO: 52, FR2 comprises SEQ ID NO: 53 and FR3 comprises SEQ ID NO: 54;

FR1 comprises SEQ ID NO: 60, FR2 comprises SEQ ID NO: 61 and FR3 comprises SEQ ID NO: 62; or FR1 comprises SEQ ID NO: 68, FR2 comprises SEQ ID NO: 69 and FR3 comprises SEQ ID NO: 70.

4. The antibody as claimed in claim 1, said amino acid sequence of formula (I) comprising an amino acid sequence selected from the group consisting of SEQ ID NO: 4, SEQ ID NO: 16, SEQ ID NO: 24, SEQ ID NO: 32, SEQ ID NO: 40, SEQ ID NO: 48, SEQ ID NO: 56, SEQ ID NO: 64 and SEQ ID NO: 72.

5. The antibody as claimed in claim 1, said antibody being chosen from a heavy chain variable domain (VH), a $V_H$H-type heavy chain variable domain ($V_H$H), a VH-type heavy-chain antibody (VH HcAb), a $V_H$H-type heavy-chain antibody ($V_H$H HcAb), a cartilaginous fish-derived anti-immunoglobulin new antigen receptor IgG heavy-chain antibody (Ig NAR) or an Ig NAR variable domain (V-NAR).

6. The antibody as claimed in claim 1, said antibody being coupled to a molecule enabling the detection of said antibody.

7. The antibody as claimed in claim 6, said molecule being chosen from a peptide tag, an enzyme, a radionuclide, a fluorescent compound, a luminescent compound, a dye, or a member of a pair of FRET partners.

8. A nucleic acid sequence coding for a single-domain antibody (sdAb) as claimed in claim 1.

9. A recombinant vector comprising the nucleic acid sequence as claimed in claim 8.

10. A cell comprising the vector as claimed in claim 9.

11. A cell comprising the nucleic acid sequence as claimed in claim 8.

* * * * *

SEQUENCE LISTING

<160> NUMBER OF SEQ ID NOS: 72

<210> SEQ ID NO 1

```
<211> LENGTH: 8
<212> TYPE: PRT
<213> ORGANISM: Artificial Sequence
<220> FEATURE:
<223> OTHER INFORMATION: F11 CDR1

<400> SEQUENCE: 1

Gly Phe Ala Phe Ser Asp Thr Trp
1               5

<210> SEQ ID NO 2
<211> LENGTH: 8
<212> TYPE: PRT
<213> ORGANISM: Artificial Sequence
<220> FEATURE:
<223> OTHER INFORMATION: F11 CDR2

<400> SEQUENCE: 2

Ile Thr Arg Gly Asp Gln Asn Thr
1               5

<210> SEQ ID NO 3
<211> LENGTH: 11
<212> TYPE: PRT
<213> ORGANISM: Artificial Sequence
<220> FEATURE:
<223> OTHER INFORMATION: F11 CDR3

<400> SEQUENCE: 3

Ala Lys Glu Gly Pro Ile Gly Pro Pro Asp Tyr
1               5                   10

<210> SEQ ID NO 4
<211> LENGTH: 143
<212> TYPE: PRT
<213> ORGANISM: Artificial Sequence
<220> FEATURE:
<223> OTHER INFORMATION: F11

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Glu Ala Ser Gly Phe Ala Phe Ser Asp Thr
            20                  25                  30

Trp Met Tyr Trp Val Arg Gln Ala Pro Gly Lys Gly Leu Glu Trp Val
        35                  40                  45

Ala Thr Ile Thr Arg Gly Asp Gln Asn Thr Tyr Tyr Thr Glu Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Val Tyr Tyr Cys
                85                  90                  95

Ala Lys Glu Gly Pro Ile Gly Pro Pro Asp Tyr Trp Gly Gln Gly Thr
            100                 105                 110

Gln Val Thr Val Ser Ser Ala Ala Glu Gln Lys Leu Ile Ser Glu
        115                 120                 125

Glu Asp Leu Asn Gly Ala Ala His His His His His Gly Ser
    130                 135                 140

<210> SEQ ID NO 5
<211> LENGTH: 25
<212> TYPE: PRT
<213> ORGANISM: Artificial Sequence
```

```
<220> FEATURE:
<223> OTHER INFORMATION: F11 FR1

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Glu Ala Ser
            20                  25

<210> SEQ ID NO 6
<211> LENGTH: 17
<212> TYPE: PRT
<213> ORGANISM: Artificial Sequence
<220> FEATURE:
<223> OTHER INFORMATION: F11 FR2

<400> SEQUENCE: 6

Met Tyr Trp Val Arg Gln Ala Pro Gly Lys Gly Leu Glu Trp Val Ala
1               5                   10                  15

Thr

<210> SEQ ID NO 7
<211> LENGTH: 38
<212> TYPE: PRT
<213> ORGANISM: Artificial Sequence
<220> FEATURE:
<223> OTHER INFORMATION: F11 FR3

<400> SEQUENCE: 7

Tyr Tyr Thr Glu Ser Val Lys Gly Arg Phe Thr Ile Ser Arg Asp Asn
1               5                   10                  15

Ala Lys Asn Thr Leu Tyr Leu Gln Met Asn Ser Leu Lys Ser Glu Asp
            20                  25                  30

Thr Ala Val Tyr Tyr Cys
        35

<210> SEQ ID NO 8
<211> LENGTH: 36
<212> TYPE: PRT
<213> ORGANISM: Artificial Sequence
<220> FEATURE:
<223> OTHER INFORMATION: F11 FR4

<400> SEQUENCE: 8

Trp Gly Gln Gly Thr Gln Val Thr Val Ser Ser Ala Ala Ala Glu Gln
1               5                   10                  15

Lys Leu Ile Ser Glu Glu Asp Leu Asn Gly Ala Ala His His His His
            20                  25                  30

His His Gly Ser
        35

<210> SEQ ID NO 9
<211> LENGTH: 8
<212> TYPE: PRT
<213> ORGANISM: Artificial Sequence
<220> FEATURE:
<223> OTHER INFORMATION: B11 CDR1

<400> SEQUENCE: 9

Gly Phe Thr Phe Asn Asp Tyr Trp
1               5

<210> SEQ ID NO 10
```

```
<211> LENGTH: 8
<212> TYPE: PRT
<213> ORGANISM: Artificial Sequence
<220> FEATURE:
<223> OTHER INFORMATION: B11 CDR2

<400> SEQUENCE: 10

Ile Asn Thr Gly Gly Ser Ser Thr
1               5

<210> SEQ ID NO 11
<211> LENGTH: 11
<212> TYPE: PRT
<213> ORGANISM: Artificial Sequence
<220> FEATURE:
<223> OTHER INFORMATION: B11 CDR3

<400> SEQUENCE: 11

Ala Lys Glu Gly Pro Val Gly Pro Pro Asp Tyr
1               5                   10

<210> SEQ ID NO 12
<211> LENGTH: 25
<212> TYPE: PRT
<213> ORGANISM: Artificial Sequence
<220> FEATURE:
<223> OTHER INFORMATION: B11 FR1

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 13
<211> LENGTH: 17
<212> TYPE: PRT
<213> ORGANISM: Artificial Sequence
<220> FEATURE:
<223> OTHER INFORMATION: B11 FR2

<400> SEQUENCE: 13

Met Tyr Trp Val Arg Gln Ala Pro Gly Lys Gly Leu Glu Trp Val Ser
1               5                   10                  15

Ser

<210> SEQ ID NO 14
<211> LENGTH: 38
<212> TYPE: PRT
<213> ORGANISM: Artificial Sequence
<220> FEATURE:
<223> OTHER INFORMATION: B11 FR3

<400> SEQUENCE: 14

Tyr Tyr Ser Asp Ser Val Lys Gly Arg Phe Thr Thr Ala Arg Asp Asn
1               5                   10                  15

Ala Lys Asn Ser Leu Tyr Leu Gln Leu Asn Ser Leu Arg Pro Glu Asp
            20                  25                  30

Thr Ala Val Tyr Tyr Cys
            35

<210> SEQ ID NO 15
<211> LENGTH: 36
<212> TYPE: PRT
<213> ORGANISM: Artificial Sequence
```

<220> FEATURE:
<223> OTHER INFORMATION: B11 FR4

<400> SEQUENCE: 15

Trp Gly Gln Gly Thr Gln Val Thr Val Ser Ser Ala Ala Glu Gln
1               5                   10                  15

Lys Leu Ile Ser Glu Glu Asp Leu Asn Gly Ala Ala His His His
            20                  25                  30

His His Gly Ser
        35

<210> SEQ ID NO 16
<211> LENGTH: 143
<212> TYPE: PRT
<213> ORGANISM: Artificial Sequence
<220> FEATURE:
<223> OTHER INFORMATION: B11

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asp Tyr
            20                  25                  30

Trp Met Tyr Trp Val Arg Gln Ala Pro Gly Lys Gly Leu Glu Trp Val
        35                  40                  45

Ser Ser Ile Asn Thr Gly Gly Ser Thr Tyr Tyr Ser Asp Ser Val
    50                  55                  60

Lys Gly Arg Phe Thr Thr Ala Arg Asp Asn Ala Lys Asn Ser Leu Tyr
65                  70                  75                  80

Leu Gln Leu Asn Ser Leu Arg Pro Glu Asp Thr Ala Val Tyr Tyr Cys
            85                  90                  95

Ala Lys Glu Gly Pro Val Gly Pro Pro Asp Tyr Trp Gly Gln Gly Thr
            100                 105                 110

Gln Val Thr Val Ser Ser Ala Ala Ala Glu Gln Lys Leu Ile Ser Glu
        115                 120                 125

Glu Asp Leu Asn Gly Ala Ala His His His His His Gly Ser
    130                 135                 140

<210> SEQ ID NO 17
<211> LENGTH: 8
<212> TYPE: PRT
<213> ORGANISM: Artificial Sequence
<220> FEATURE:
<223> OTHER INFORMATION: F9 CDR1

<400> SEQUENCE: 17

Gly Phe Thr Phe Asp Asp Tyr Ala
1               5

<210> SEQ ID NO 18
<211> LENGTH: 8
<212> TYPE: PRT
<213> ORGANISM: Artificial Sequence
<220> FEATURE:
<223> OTHER INFORMATION: F9 CDR2

<400> SEQUENCE: 18

Ile Ser Ser Arg Gly Ile Thr Thr
1               5

<210> SEQ ID NO 19

-continued

```
<211> LENGTH: 13
<212> TYPE: PRT
<213> ORGANISM: Artificial Sequence
<220> FEATURE:
<223> OTHER INFORMATION: F9 CDR3

<400> SEQUENCE: 19

Ala Thr Asp Pro Ser Thr Trp Tyr Arg Gly Thr Ala His
1               5                   10

<210> SEQ ID NO 20
<211> LENGTH: 25
<212> TYPE: PRT
<213> ORGANISM: Artificial Sequence
<220> FEATURE:
<223> OTHER INFORMATION: F9 FR1

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 21
<211> LENGTH: 17
<212> TYPE: PRT
<213> ORGANISM: Artificial Sequence
<220> FEATURE:
<223> OTHER INFORMATION: F9 FR2

<400> SEQUENCE: 21

Met Asn Trp Val Arg Gln Ala Ala Gly Lys Gly Pro Glu Trp Val Ala
1               5                   10                  15

Ser

<210> SEQ ID NO 22
<211> LENGTH: 38
<212> TYPE: PRT
<213> ORGANISM: Artificial Sequence
<220> FEATURE:
<223> OTHER INFORMATION: F9 FR3

<400> SEQUENCE: 22

Asp Tyr Ala His Ser Val Lys Gly Arg Phe Thr Val Ser Arg Asp Asn
1               5                   10                  15

Thr Lys Asn Thr Leu Tyr Leu Gln Met Asn Ser Leu Lys Pro Asp Asp
            20                  25                  30

Ala Ala Val Tyr Tyr Cys
            35

<210> SEQ ID NO 23
<211> LENGTH: 36
<212> TYPE: PRT
<213> ORGANISM: Artificial Sequence
<220> FEATURE:
<223> OTHER INFORMATION: F9 FR4

<400> SEQUENCE: 23

Trp Gly Gln Gly Thr Gln Val Thr Val Ser Ser Ala Ala Ala Glu Gln
1               5                   10                  15

Lys Leu Ile Ser Glu Glu Asp Leu Asn Gly Ala Ala His His His His
            20                  25                  30

His His Gly Ser
            35
```

<210> SEQ ID NO 24
<211> LENGTH: 145
<212> TYPE: PRT
<213> ORGANISM: Artificial Sequence
<220> FEATURE:
<223> OTHER INFORMATION: F9

<400> SEQUENCE: 24

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Met Asn Trp Val Arg Gln Ala Ala Gly Lys Gly Pro Glu Trp Val
        35                  40                  45

Ala Ser Ile Ser Ser Arg Gly Ile Thr Thr Asp Tyr Ala His Ser Val
    50                  55                  60

Lys Gly Arg Phe Thr Val Ser Arg Asp Asn Thr Lys Asn Thr Leu Tyr
65                  70                  75                  80

Leu Gln Met Asn Ser Leu Lys Pro Asp Asp Ala Val Tyr Tyr Cys
                85                  90                  95

Ala Thr Asp Pro Ser Thr Trp Tyr Arg Gly Thr Ala His Trp Gly Gln
            100                 105                 110

Gly Thr Gln Val Thr Val Ser Ser Ala Ala Glu Gln Lys Leu Ile
        115                 120                 125

Ser Glu Glu Asp Leu Asn Gly Ala Ala His His His His His His Gly
    130                 135                 140

Ser
145
```

<210> SEQ ID NO 25
<211> LENGTH: 8
<212> TYPE: PRT
<213> ORGANISM: Artificial Sequence
<220> FEATURE:
<223> OTHER INFORMATION: G6 CDR1

<400> SEQUENCE: 25

```
Gly Phe Thr Phe Ser Thr Tyr Arg
1               5
```

<210> SEQ ID NO 26
<211> LENGTH: 8
<212> TYPE: PRT
<213> ORGANISM: Artificial Sequence
<220> FEATURE:
<223> OTHER INFORMATION: G6 CDR2

<400> SEQUENCE: 26

```
Ile Ser Ser Arg Gly Ile Thr Thr
1               5
```

<210> SEQ ID NO 27
<211> LENGTH: 13
<212> TYPE: PRT
<213> ORGANISM: Artificial Sequence
<220> FEATURE:
<223> OTHER INFORMATION: G6 CDR3

<400> SEQUENCE: 27

```
Ala Thr Asp Pro Ser Thr Trp Tyr Arg Gly Thr Ala His
1               5                   10
```

<210> SEQ ID NO 28
<211> LENGTH: 25
<212> TYPE: PRT
<213> ORGANISM: Artificial Sequence
<220> FEATURE:
<223> OTHER INFORMATION: G6 FR1

<400> SEQUENCE: 28

Glu Val Gln Leu Val Glu Ser Gly Gly Asp Leu Val Gln Pro Gly Gly
1               5                   10                  15

Ser Leu Arg Leu Ser Cys Ala Ala Ser
            20                  25

<210> SEQ ID NO 29
<211> LENGTH: 17
<212> TYPE: PRT
<213> ORGANISM: Artificial Sequence
<220> FEATURE:
<223> OTHER INFORMATION: G6 FR2

<400> SEQUENCE: 29

Met Asn Trp Val Arg Gln Ala Pro Gly Lys Gly Leu Glu Trp Val Ala
1               5                   10                  15

Ser

<210> SEQ ID NO 30
<211> LENGTH: 38
<212> TYPE: PRT
<213> ORGANISM: Artificial Sequence
<220> FEATURE:
<223> OTHER INFORMATION: G6 FR3

<400> SEQUENCE: 30

Asp Tyr Ala His Pro Val Lys Gly Arg Phe Thr Val Ser Arg Asp Asn
1               5                   10                  15

Thr Lys Asn Thr Leu Tyr Leu Gln Met Asn Ser Leu Lys Pro Asp Asp
            20                  25                  30

Ala Ala Val Tyr Tyr Cys
        35

<210> SEQ ID NO 31
<211> LENGTH: 36
<212> TYPE: PRT
<213> ORGANISM: Artificial Sequence
<220> FEATURE:
<223> OTHER INFORMATION: G6 FR4

<400> SEQUENCE: 31

Trp Gly Gln Gly Thr Gln Val Thr Val Ser Ser Ala Ala Ala Glu Gln
1               5                   10                  15

Lys Leu Ile Ser Glu Glu Asp Leu Asn Gly Ala Ala His His His His
            20                  25                  30

His His Gly Ser
        35

<210> SEQ ID NO 32
<211> LENGTH: 145
<212> TYPE: PRT
<213> ORGANISM: Artificial Sequence
<220> FEATURE:
<223> OTHER INFORMATION: G6

<400> SEQUENCE: 32

```
Glu Val Gln Leu Val Glu Ser Gly Gly Asp Leu Val Gln Pro Gly Gly
1               5                   10                  15

Ser Leu Arg Leu Ser Cys Ala Ala Ser Gly Phe Thr Phe Ser Thr Tyr
            20                  25                  30

Arg Met Asn Trp Val Arg Gln Ala Pro Gly Lys Gly Leu Glu Trp Val
        35                  40                  45

Ala Ser Ile Ser Ser Arg Gly Ile Thr Thr Asp Tyr Ala His Pro Val
    50                  55                  60

Lys Gly Arg Phe Thr Val Ser Arg Asp Asn Thr Lys Asn Thr Leu Tyr
65                  70                  75                  80

Leu Gln Met Asn Ser Leu Lys Pro Asp Asp Ala Ala Val Tyr Tyr Cys
                85                  90                  95

Ala Thr Asp Pro Ser Thr Trp Tyr Arg Gly Thr Ala His Trp Gly Gln
            100                 105                 110

Gly Thr Gln Val Thr Val Ser Ser Ala Ala Ala Glu Gln Lys Leu Ile
        115                 120                 125

Ser Glu Glu Asp Leu Asn Gly Ala Ala His His His His His His Gly
    130                 135                 140

Ser
145

<210> SEQ ID NO 33
<211> LENGTH: 8
<212> TYPE: PRT
<213> ORGANISM: Artificial Sequence
<220> FEATURE:
<223> OTHER INFORMATION: F4 CDR1

<400> SEQUENCE: 33

Gly Phe Thr Phe Ser Ser Tyr Tyr
1               5

<210> SEQ ID NO 34
<211> LENGTH: 8
<212> TYPE: PRT
<213> ORGANISM: Artificial Sequence
<220> FEATURE:
<223> OTHER INFORMATION: F4 CDR2

<400> SEQUENCE: 34

Ile Tyr Asn Gly Asp Gly Asp Thr
1               5

<210> SEQ ID NO 35
<211> LENGTH: 11
<212> TYPE: PRT
<213> ORGANISM: Artificial Sequence
<220> FEATURE:
<223> OTHER INFORMATION: F4 CDR3

<400> SEQUENCE: 35

Asn Ala Tyr Asp Gly Thr Leu Leu Arg Asp Tyr
1               5                   10

<210> SEQ ID NO 36
<211> LENGTH: 25
<212> TYPE: PRT
<213> ORGANISM: Artificial Sequence
<220> FEATURE:
<223> OTHER INFORMATION: F4 FR1

<400> SEQUENCE: 36
```

```
Glu Val Gln Leu Val Glu Ser Gly Gly Gly Leu Val Gln Pro Gly Gly
1               5                   10                  15

Ser Leu Arg Leu Ser Cys Ala Ala Ser
                20                  25

<210> SEQ ID NO 37
<211> LENGTH: 17
<212> TYPE: PRT
<213> ORGANISM: Artificial Sequence
<220> FEATURE:
<223> OTHER INFORMATION: F4 FR2

<400> SEQUENCE: 37

Met Asn Trp Val Arg Gln Ala Pro Gly Lys Gly Leu Glu Trp Val Ser
1               5                   10                  15

Ser

<210> SEQ ID NO 38
<211> LENGTH: 38
<212> TYPE: PRT
<213> ORGANISM: Artificial Sequence
<220> FEATURE:
<223> OTHER INFORMATION: F4 FR3

<400> SEQUENCE: 38

Asp Tyr Ser Asp Ser Val Lys Gly Arg Phe Thr Ile Ser Arg Asp Asn
1               5                   10                  15

Ala Lys Asn Thr Val Tyr Leu Glu Met Ser Asp Leu Lys Val Gln Asp
                20                  25                  30

Thr Ala Ile Tyr Tyr Cys
            35

<210> SEQ ID NO 39
<211> LENGTH: 36
<212> TYPE: PRT
<213> ORGANISM: Artificial Sequence
<220> FEATURE:
<223> OTHER INFORMATION: F4 FR4

<400> SEQUENCE: 39

Trp Gly Gln Gly Thr Gln Val Thr Val Ser Ser Ala Ala Ala Glu Gln
1               5                   10                  15

Lys Leu Ile Ser Glu Glu Asp Leu Asn Gly Ala Ala His His His His
                20                  25                  30

His His Gly Ser
            35

<210> SEQ ID NO 40
<211> LENGTH: 143
<212> TYPE: PRT
<213> ORGANISM: Artificial Sequence
<220> FEATURE:
<223> OTHER INFORMATION: F4

<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Tyr Met Asn Trp Val Arg Gln Ala Pro Gly Lys Gly Leu Glu Trp Val
            35                  40                  45
```

-continued

```
Ser Ser Ile Tyr Asn Gly Asp Gly Asp Thr Asp Tyr Ser Asp Ser Val
        50                  55                  60
Lys Gly Arg Phe Thr Ile Ser Arg Asp Asn Ala Lys Asn Thr Val Tyr
 65                  70                  75                  80
Leu Glu Met Ser Asp Leu Lys Val Gln Asp Thr Ala Ile Tyr Tyr Cys
                 85                  90                  95
Asn Ala Tyr Asp Gly Thr Leu Leu Arg Asp Tyr Trp Gly Gln Gly Thr
             100                 105                 110
Gln Val Thr Val Ser Ser Ala Ala Glu Gln Lys Leu Ile Ser Glu
            115                 120                 125
Glu Asp Leu Asn Gly Ala Ala His His His His His Gly Ser
130                 135                 140
```

<210> SEQ ID NO 41
<211> LENGTH: 8
<212> TYPE: PRT
<213> ORGANISM: Artificial Sequence
<220> FEATURE:
<223> OTHER INFORMATION: A10 CDR1

<400> SEQUENCE: 41

```
Gly Leu Thr Tyr Ser Asp Tyr Ala
1               5
```

<210> SEQ ID NO 42
<211> LENGTH: 8
<212> TYPE: PRT
<213> ORGANISM: Artificial Sequence
<220> FEATURE:
<223> OTHER INFORMATION: A10 CDR2

<400> SEQUENCE: 42

```
Ile Ser Ser Arg Gly Ile Thr Thr
1               5
```

<210> SEQ ID NO 43
<211> LENGTH: 10
<212> TYPE: PRT
<213> ORGANISM: Artificial Sequence
<220> FEATURE:
<223> OTHER INFORMATION: A10 CDR3

<400> SEQUENCE: 43

```
Thr Thr Val Ser Tyr Trp Arg Tyr Glu Tyr
1               5                  10
```

<210> SEQ ID NO 44
<211> LENGTH: 25
<212> TYPE: PRT
<213> ORGANISM: Artificial Sequence
<220> FEATURE:
<223> OTHER INFORMATION: A10 FR1

<400> SEQUENCE: 44

```
Glu Val Gln Leu Val Glu Ser Gly Gly Gly Leu Val Gln Pro Gly Gly
1               5                  10                  15
Ser Leu Arg Leu Ser Cys Ala Ala Ser
            20                  25
```

<210> SEQ ID NO 45
<211> LENGTH: 17
<212> TYPE: PRT
<213> ORGANISM: Artificial Sequence
<220> FEATURE:

<223> OTHER INFORMATION: A10 FR2

<400> SEQUENCE: 45

Met Ser Trp Val Arg Gln Ala Ala Gly Lys Gly Pro Glu Trp Val Ala
1               5                   10                  15

Ser

<210> SEQ ID NO 46
<211> LENGTH: 38
<212> TYPE: PRT
<213> ORGANISM: Artificial Sequence
<220> FEATURE:
<223> OTHER INFORMATION: A10 FR3

<400> SEQUENCE: 46

Asp Tyr Ala His Ser Val Lys Gly Arg Phe Thr Val Ser Arg Asp Asn
1               5                   10                  15

Thr Lys Asn Thr Leu Tyr Leu Gln Met Asn Ser Leu Glu Pro Glu Asp
            20                  25                  30

Thr Ala Val Tyr Tyr Cys
        35

<210> SEQ ID NO 47
<211> LENGTH: 36
<212> TYPE: PRT
<213> ORGANISM: Artificial Sequence
<220> FEATURE:
<223> OTHER INFORMATION: A10 FR4

<400> SEQUENCE: 47

Trp Gly Gln Gly Thr Gln Val Thr Val Ser Ser Ala Ala Ala Glu Gln
1               5                   10                  15

Lys Leu Ile Ser Glu Glu Asp Leu Asn Gly Ala Ala His His His His
            20                  25                  30

His His Gly Ser
        35

<210> SEQ ID NO 48
<211> LENGTH: 142
<212> TYPE: PRT
<213> ORGANISM: Artificial Sequence
<220> FEATURE:
<223> OTHER INFORMATION: A10

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Tyr Ser Asp Tyr
            20                  25                  30

Ala Met Ser Trp Val Arg Gln Ala Ala Gly Lys Gly Pro Glu Trp Val
        35                  40                  45

Ala Ser Ile Ser Ser Arg Gly Ile Thr Thr Asp Tyr Ala His Ser Val
    50                  55                  60

Lys Gly Arg Phe Thr Val Ser Arg Asp Asn Thr Lys Asn Thr Leu Tyr
65                  70                  75                  80

Leu Gln Met Asn Ser Leu Glu Pro Glu Asp Thr Ala Val Tyr Tyr Cys
                85                  90                  95

Thr Thr Val Ser Tyr Trp Arg Tyr Glu Tyr Trp Gly Gln Gly Thr Gln
            100                 105                 110

Val Thr Val Ser Ser Ala Ala Ala Glu Gln Lys Leu Ile Ser Glu Glu

```
              115                 120                 125
Asp Leu Asn Gly Ala Ala His His His His His Gly Ser
            130                 135                 140

<210> SEQ ID NO 49
<211> LENGTH: 8
<212> TYPE: PRT
<213> ORGANISM: Artificial Sequence
<220> FEATURE:
<223> OTHER INFORMATION: F2 CDR1

<400> SEQUENCE: 49

Gly Phe Thr Phe Ser Ser Tyr Ala
1               5

<210> SEQ ID NO 50
<211> LENGTH: 8
<212> TYPE: PRT
<213> ORGANISM: Artificial Sequence
<220> FEATURE:
<223> OTHER INFORMATION: F2 CDR2

<400> SEQUENCE: 50

Ile Ser Ser Arg Gly Ile Thr Thr
1               5

<210> SEQ ID NO 51
<211> LENGTH: 8
<212> TYPE: PRT
<213> ORGANISM: Artificial Sequence
<220> FEATURE:
<223> OTHER INFORMATION: F2 CDR3

<400> SEQUENCE: 51

Val Lys Gly Trp Met Pro Thr Gly
1               5

<210> SEQ ID NO 52
<211> LENGTH: 25
<212> TYPE: PRT
<213> ORGANISM: Artificial Sequence
<220> FEATURE:
<223> OTHER INFORMATION: F2 FR1

<400> SEQUENCE: 52

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 53
<211> LENGTH: 17
<212> TYPE: PRT
<213> ORGANISM: Artificial Sequence
<220> FEATURE:
<223> OTHER INFORMATION: F2 FR2

<400> SEQUENCE: 53

Met Ser Trp Val Arg Gln Ala Ala Gly Lys Gly Pro Glu Trp Val Ala
1               5                   10                  15

Ser

<210> SEQ ID NO 54
<211> LENGTH: 38
<212> TYPE: PRT
```

<213> ORGANISM: Artificial Sequence
<220> FEATURE:
<223> OTHER INFORMATION: F2 FR3

<400> SEQUENCE: 54

Asp Tyr Ala His Ser Val Lys Gly Arg Phe Thr Val Ser Arg Asp Asn
1               5                   10                  15

Thr Lys Asn Thr Leu Tyr Leu Gln Met Asn Ser Leu Lys Pro Glu Asp
            20                  25                  30

Thr Ala Leu Tyr Tyr Cys
        35

<210> SEQ ID NO 55
<211> LENGTH: 36
<212> TYPE: PRT
<213> ORGANISM: Artificial Sequence
<220> FEATURE:
<223> OTHER INFORMATION: F2 FR4

<400> SEQUENCE: 55

Trp Gly Gln Gly Thr Gln Val Thr Val Ser Ser Ala Ala Ala Glu Gln
1               5                   10                  15

Lys Leu Ile Ser Glu Glu Asp Leu Asn Gly Ala Ala His His His His
            20                  25                  30

His His Gly Ser
        35

<210> SEQ ID NO 56
<211> LENGTH: 140
<212> TYPE: PRT
<213> ORGANISM: Artificial Sequence
<220> FEATURE:
<223> OTHER INFORMATION: F2

<400> SEQUENCE: 56

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Ala Gly Lys Gly Pro Glu Trp Val
        35                  40                  45

Ala Ser Ile Ser Ser Arg Gly Ile Thr Thr Asp Tyr Ala His Ser Val
    50                  55                  60

Lys Gly Arg Phe Thr Val Ser Arg Asp Asn Thr Lys Asn Thr Leu Tyr
65                  70                  75                  80

Leu Gln Met Asn Ser Leu Lys Pro Glu Asp Thr Ala Leu Tyr Tyr Cys
                85                  90                  95

Val Lys Gly Trp Met Pro Thr Gly Trp Gly Gln Gly Thr Gln Val Thr
            100                 105                 110

Val Ser Ser Ala Ala Ala Glu Gln Lys Leu Ile Ser Glu Glu Asp Leu
        115                 120                 125

Asn Gly Ala Ala His His His His His Gly Ser
    130                 135                 140

<210> SEQ ID NO 57
<211> LENGTH: 8
<212> TYPE: PRT
<213> ORGANISM: Artificial Sequence
<220> FEATURE:
<223> OTHER INFORMATION: E2 CDR1

```
<400> SEQUENCE: 57

Gly Tyr Thr Phe Ser Ser Tyr Ala
1               5

<210> SEQ ID NO 58
<211> LENGTH: 8
<212> TYPE: PRT
<213> ORGANISM: Artificial Sequence
<220> FEATURE:
<223> OTHER INFORMATION: E2 CDR2

<400> SEQUENCE: 58

Ile Ser Ser Arg Gly Ile Thr Thr
1               5

<210> SEQ ID NO 59
<211> LENGTH: 16
<212> TYPE: PRT
<213> ORGANISM: Artificial Sequence
<220> FEATURE:
<223> OTHER INFORMATION: E2 CDR3

<400> SEQUENCE: 59

Thr Arg Val Leu Trp Tyr Glu Asn Gly Leu Tyr Ser Leu Asn Asp Phe
1               5                   10                  15

<210> SEQ ID NO 60
<211> LENGTH: 25
<212> TYPE: PRT
<213> ORGANISM: Artificial Sequence
<220> FEATURE:
<223> OTHER INFORMATION: E2 FR1

<400> SEQUENCE: 60

Glu Val Gln Leu Val Glu Ser Gly Gly Gly Leu Val Gln Pro Gly Gly
1               5                   10                  15

Ser Leu Arg Leu Ser Cys Ile Gly Ser
            20                  25

<210> SEQ ID NO 61
<211> LENGTH: 17
<212> TYPE: PRT
<213> ORGANISM: Artificial Sequence
<220> FEATURE:
<223> OTHER INFORMATION: E2 FR2

<400> SEQUENCE: 61

Met Ala Trp Val Arg Gln Ala Ser Gly Lys Gly Pro Glu Trp Val Ala
1               5                   10                  15

Ser

<210> SEQ ID NO 62
<211> LENGTH: 38
<212> TYPE: PRT
<213> ORGANISM: Artificial Sequence
<220> FEATURE:
<223> OTHER INFORMATION: E2 FR3

<400> SEQUENCE: 62

Asp Tyr Ala His Ser Val Lys Gly Arg Phe Thr Ile Ser Arg Asp Asn
1               5                   10                  15

Ala Lys Asn Thr Leu Tyr Leu His Met Asn Asn Leu Lys Pro Glu Asp
            20                  25                  30

Thr Ala Leu Tyr Tyr Cys
```

<210> SEQ ID NO 63
<211> LENGTH: 36
<212> TYPE: PRT
<213> ORGANISM: Artificial Sequence
<220> FEATURE:
<223> OTHER INFORMATION: E2 FR4

<400> SEQUENCE: 63

Trp Gly Gln Gly Thr Gln Val Thr Val Ser Ser Ala Ala Ala Glu Gln
1               5                   10                  15

Lys Leu Ile Ser Glu Glu Asp Leu Asn Gly Ala Ala His His His His
            20                  25                  30

His His Gly Ser
        35

<210> SEQ ID NO 64
<211> LENGTH: 148
<212> TYPE: PRT
<213> ORGANISM: Artificial Sequence
<220> FEATURE:
<223> OTHER INFORMATION: E2

<400> SEQUENCE: 64

Glu Val Gln Leu Val Glu Ser Gly Gly Leu Val Gln Pro Gly Gly
1               5                   10                  15

Ser Leu Arg Leu Ser Cys Ile Gly Ser Gly Tyr Thr Phe Ser Ser Tyr
            20                  25                  30

Ala Met Ala Trp Val Arg Gln Ala Ser Gly Lys Gly Pro Glu Trp Val
        35                  40                  45

Ala Ser Ile Ser Ser Arg Gly Ile Thr Thr Asp Tyr Ala His Ser Val
    50                  55                  60

Lys Gly Arg Phe Thr Ile Ser Arg Asp Asn Ala Lys Asn Thr Leu Tyr
65                  70                  75                  80

Leu His Met Asn Asn Leu Lys Pro Glu Asp Thr Ala Leu Tyr Tyr Cys
                85                  90                  95

Thr Arg Val Leu Trp Tyr Glu Asn Gly Leu Tyr Ser Leu Asn Asp Phe
            100                 105                 110

Trp Gly Gln Gly Thr Gln Val Thr Val Ser Ser Ala Ala Ala Glu Gln
        115                 120                 125

Lys Leu Ile Ser Glu Glu Asp Leu Asn Gly Ala Ala His His His His
    130                 135                 140

His His Gly Ser
145

<210> SEQ ID NO 65
<211> LENGTH: 8
<212> TYPE: PRT
<213> ORGANISM: Artificial Sequence
<220> FEATURE:
<223> OTHER INFORMATION: G7 CDR1

<400> SEQUENCE: 65

Gly Phe Thr Phe Ser Trp Tyr Gly
1               5

<210> SEQ ID NO 66
<211> LENGTH: 8
<212> TYPE: PRT
<213> ORGANISM: Artificial Sequence

```
<220> FEATURE:
<223> OTHER INFORMATION: G7 CDR2

<400> SEQUENCE: 66

Ile Ser Ser Arg Gly Ile Thr Thr
1               5

<210> SEQ ID NO 67
<211> LENGTH: 16
<212> TYPE: PRT
<213> ORGANISM: Artificial Sequence
<220> FEATURE:
<223> OTHER INFORMATION: G7 CDR3

<400> SEQUENCE: 67

Thr Arg Val Leu Trp Tyr Asp Ser Gly Ala Tyr Ser Leu Asn Asp Phe
1               5                   10                  15

<210> SEQ ID NO 68
<211> LENGTH: 25
<212> TYPE: PRT
<213> ORGANISM: Artificial Sequence
<220> FEATURE:
<223> OTHER INFORMATION: G7 FR1

<400> SEQUENCE: 68

Gln Val Gln Leu Gln Glu Ser Gly Gly Gly Leu Val Gln Pro Gly Gly
1               5                   10                  15

Ser Leu Arg Leu Ser Cys Ala Ala Ser
            20                  25

<210> SEQ ID NO 69
<211> LENGTH: 17
<212> TYPE: PRT
<213> ORGANISM: Artificial Sequence
<220> FEATURE:
<223> OTHER INFORMATION: G7 FR2

<400> SEQUENCE: 69

Met Ser Trp Val Arg Gln Ala Pro Gly Lys Gly Pro Glu Trp Val Ala
1               5                   10                  15

Ser

<210> SEQ ID NO 70
<211> LENGTH: 38
<212> TYPE: PRT
<213> ORGANISM: Artificial Sequence
<220> FEATURE:
<223> OTHER INFORMATION: G7 FR3

<400> SEQUENCE: 70

Asp Tyr Ala His Ser Val Lys Gly Arg Phe Thr Val Ser Arg Asp Asn
1               5                   10                  15

Thr Lys Asn Thr Leu Tyr Leu Gln Met Asn Ser Leu Lys Pro Glu Asp
            20                  25                  30

Thr Gly Val Tyr Tyr Cys
        35

<210> SEQ ID NO 71
<211> LENGTH: 36
<212> TYPE: PRT
<213> ORGANISM: Artificial Sequence
<220> FEATURE:
<223> OTHER INFORMATION: G7 FR4
```

```
<400> SEQUENCE: 71

Trp Gly Gln Gly Thr Gln Val Thr Val Ser Ser Ala Ala Ala Glu Gln
1               5                   10                  15

Lys Leu Ile Ser Glu Glu Asp Leu Asn Gly Ala Ala His His His His
            20                  25                  30

His His Gly Ser
        35

<210> SEQ ID NO 72
<211> LENGTH: 148
<212> TYPE: PRT
<213> ORGANISM: Artificial Sequence
<220> FEATURE:
<223> OTHER INFORMATION: G7

<400> SEQUENCE: 72

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Gly Met Ser Trp Val Arg Gln Ala Pro Gly Lys Gly Pro Glu Trp Val
        35                  40                  45

Ala Ser Ile Ser Ser Arg Gly Ile Thr Thr Asp Tyr Ala His Ser Val
    50                  55                  60

Lys Gly Arg Phe Thr Val Ser Arg Asp Asn Thr Lys Asn Thr Leu Tyr
65                  70                  75                  80

Leu Gln Met Asn Ser Leu Lys Pro Glu Asp Thr Gly Val Tyr Tyr Cys
                85                  90                  95

Thr Arg Val Leu Trp Tyr Asp Ser Gly Ala Tyr Ser Leu Asn Asp Phe
            100                 105                 110

Trp Gly Gln Gly Thr Gln Val Thr Val Ser Ser Ala Ala Ala Glu Gln
        115                 120                 125

Lys Leu Ile Ser Glu Glu Asp Leu Asn Gly Ala Ala His His His His
    130                 135                 140

His His Gly Ser
145
```